United States Patent
Hou et al.

(10) Patent No.: US 8,412,327 B2
(45) Date of Patent: Apr. 2, 2013

(54) CARDIAC RESYNCHRONIZATION THERAPY OPTIMIZATION USING VECTOR MEASUREMENTS OBTAINED FROM REALTIME ELECTRODE POSITION TRACKING

(75) Inventors: Wenbo Hou, Lancaster, CA (US); Stuart Rosenberg, Castaic, CA (US); Kyungmoo Ryu, Palmdale, CA (US); Allen Keel, San Francisco, CA (US); Steve Koh, South Pasadena, CA (US); Thao Thu Nguyen, Bloomington, MN (US); Kjell Noren, Solna (SE); Michael Yang, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 380 days.

(21) Appl. No.: 12/621,397

(22) Filed: Nov. 18, 2009

(65) Prior Publication Data
US 2011/0118803 A1 May 19, 2011

(51) Int. Cl.
*A61N 1/365* (2006.01)
(52) U.S. Cl. ........................................................ 607/17
(58) Field of Classification Search .................... 607/17; 600/509
See application file for complete search history.

(56) References Cited

U.S. PATENT DOCUMENTS

| | | | |
|---|---|---|---|
| 6,990,370 B1 * | 1/2006 | Beatty et al. | 600/509 |
| 2003/0204214 A1 * | 10/2003 | Ferek-Patric | 607/27 |
| 2005/0228276 A1 * | 10/2005 | He et al. | 600/437 |
| 2006/0253164 A1 * | 11/2006 | Zhang et al. | 607/28 |
| 2008/0183072 A1 * | 7/2008 | Robertson et al. | 600/425 |
| 2008/0294218 A1 * | 11/2008 | Savage et al. | 607/30 |
| 2009/0093857 A1 | 4/2009 | Markowitz et al. | |

FOREIGN PATENT DOCUMENTS
WO 2007111542 A1 10/2007

* cited by examiner

*Primary Examiner* — Carl H Layno
*Assistant Examiner* — Paul J Stice

(57) ABSTRACT

An exemplary method includes selecting a first pair of electrodes to define a first vector and selecting a second pair of electrodes to define a second vector; acquiring position information during one or more cardiac cycles for the first and second pairs of electrodes wherein the acquiring comprises using each of the electrodes for measuring one or more electrical potentials in an electrical localization field established in the patient; and determining a dyssynchrony index by applying a cross-covariance technique to the position information for the first and the second vectors. Another method includes determining a phase shift based on the acquired position information for the first and the second vectors; and determining an interventricular delay based at least in part on the phase shift.

18 Claims, 20 Drawing Sheets

CARDIAC RESYNCHRONIZATION THERAPY OPTIMIZATION USING VECTOR MEASUREMENTS OBTAINED FROM REALTIME ELECTRODE POSITION TRACKING

TECHNICAL FIELD

Subject matter presented herein relates generally to electrode and lead-based investigation or therapy systems (e.g., cardiac pacing therapies, cardiac stimulation therapies, etc.). Various examples acquire position data using a localization system and, based on the acquired data, calculate metrics for assessing cardiac condition and for optimizing cardiac therapy.

BACKGROUND

Cardiac resynchronization therapy (CRT) aims to improve cardiac performance by synchronizing the ventricles. While the term "synchronization" is used, for some patients, a delay between contraction of the right ventricle and the left ventricle may be optimal. Hence, the term synchronization refers more generally to ventricular timing that improves cardiac performance. A general objective measure of lack of synchrony or dyssynchrony is QRS width representative of contraction of both ventricles. For example, a QRS width greater than about 130 ms may indicate dyssynchrony.

CRT can improve a variety of cardiac performance measures including left ventricular mechanical function, cardiac index, decreased pulmonary artery pressures, decrease in myocardial oxygen consumption, decrease in dynamic mitral regurgitation, increase in global ejection fraction, decrease in NYHA class, increased quality of life scores, increased distance covered during a 6-minute walk test, etc. Effects such as reverse modeling may also be seen, for example, three to six months after initiating CRT. Patients that show such improvements are classified as CRT "responders". However, for a variety of reasons, not all patients respond to CRT. For example, if a left ventricular stimulation lead cannot locate an electrode in a favorable position, then a patient may not respond to CRT.

Often, the ability to respond and the extent of response to CRT depends on an initial set-up of a CRT device in a patient. As described herein, various exemplary technologies aim to improve a clinician's ability to set-up a CRT at implant and to optionally optimize thereafter. In particular, various exemplary techniques include vector metrics based, at least in part, on information acquired from a localization system.

SUMMARY

An exemplary method includes selecting a first pair of electrodes to define a first vector and selecting a second pair of electrodes to define a second vector; acquiring position information during one or more cardiac cycles for the first and second pairs of electrodes wherein the acquiring comprises using each of the electrodes for measuring one or more electrical potentials in an electrical localization field established in the patient; and determining a dyssynchrony index by applying a cross-covariance technique to the position information for the first and the second vectors. Another method includes determining a phase shift based on the acquired position information for the first and the second vectors; and determining an interventricular delay based at least in part on the phase shift.

BRIEF DESCRIPTION OF THE DRAWINGS

Features and advantages of the described implementations can be more readily understood by reference to the following description taken in conjunction with the accompanying drawings.

DETAILED DESCRIPTION

Figure 1:
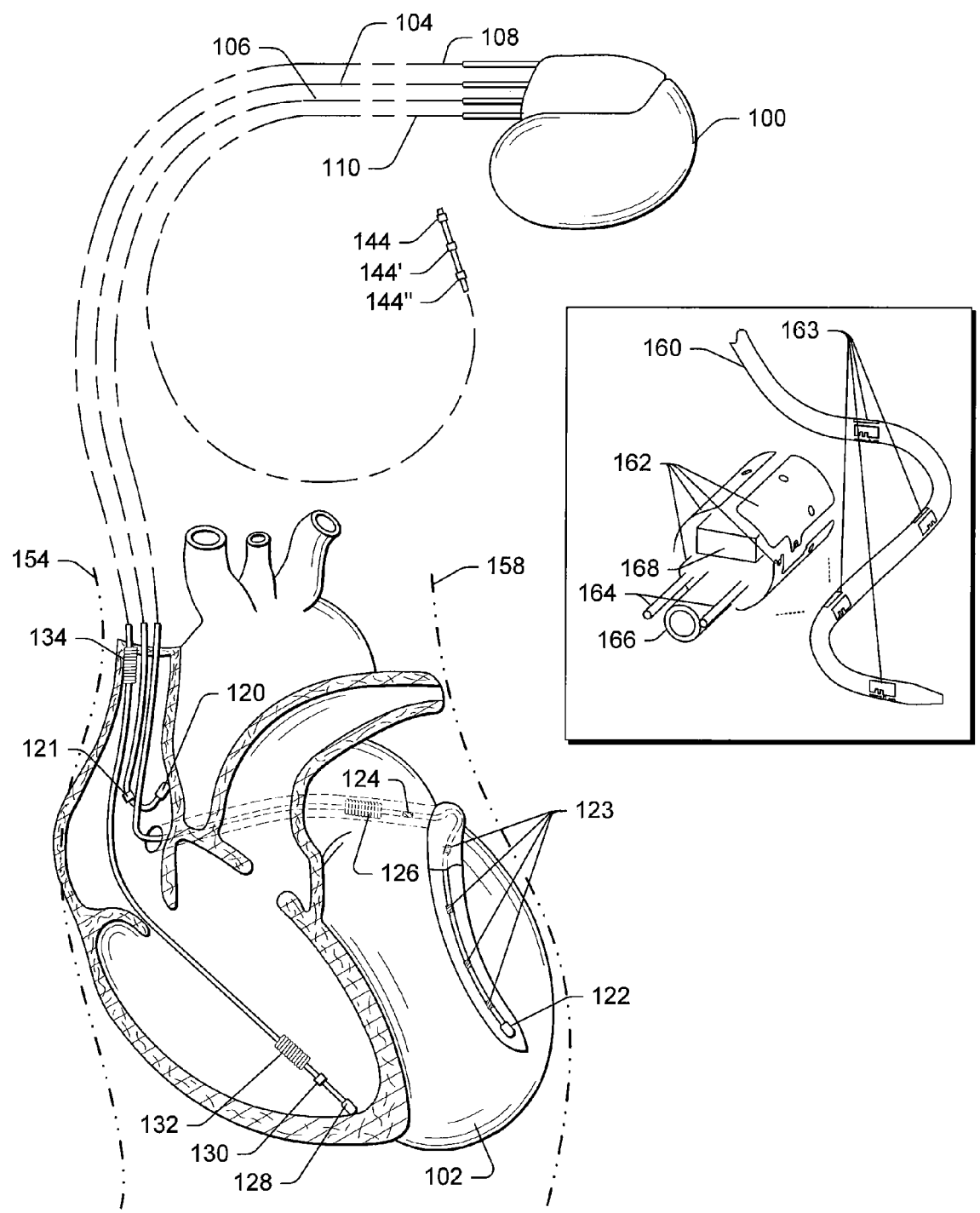
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are typically used to reference like parts or elements throughout.

Overview

Various exemplary techniques described herein pertain to analysis of electrode positions in the body. For example, during an intraoperative procedure, a clinician may maneuver an electrode-bearing catheter to various locations in one or more chambers or vessels of the heart and acquire position information sufficient to calculate one or more metrics. As described below, such metrics include vector-based metrics and other metrics based in part on electrode position (e.g., position dispersion metrics). In various examples, acquisition of position information may occur for an acute state, a chronic state or an acute state and a chronic state, for example, sufficient to calculated one or more state metrics. As described herein, various metrics are referred to as indexes. For example, a dyssynchrony index can be calculated based on magnitude or angle waveforms for a right ventricular vector and a left ventricular vector. Such a dyssynchrony index may be an interventricular dyssynchrony index. Other types of vector-based indexes include, for example, an intraventricular dyssynchrony index, an interatrial dyssynchrony index, an intraatrial dyssynchrony index and an interatrioventricular dyssynchrony index. As described herein, various exemplary vector analysis techniques include statistical techniques such as correlation or cross-covariance. Accordingly, therapy configuration, parameters or configuration and parameters may be determined and optimized using one or more exemplary vector-based methods.

Various exemplary methods may be implemented, for example, using a pacing system analyzer (PSA) and a localization system or a specialized localization system. Various examples are described with respect to the ENSITE® NAVX® localization system (St Jude Medical, Inc., Minnesota); noting that other types of localization systems may be used.

Various techniques aim to facilitate lead implants, particularly for leads that enter the coronary sinus to reach distal branches thereof. For example, a clinician can view plots or maps of one or more metrics and readily decide to locate a lead in a region with acceptable or optimal metrics for delivery of a cardiac therapy. A typical intraoperative, acute state process occurs iteratively (i.e., select or move, acquire, calculate; select or move, acquire, calculate; ...). In this iterative process, a clinician may note whether a location has acceptable metrics or unacceptable metrics.

As described herein, various techniques can calculate vector metrics and generate information for display (e.g., data tables, plots, maps, etc.) to aid a clinician. Various techniques may operate in conjunction with one or more PSA functionalities, for example, to create and display maps that show variations in metrics with respect to anatomic features. Various exemplary methods include analyzing one or more vector metrics to optimize pacing mode for maximum cardiac contractility. For example, as described in more detail below, various animal and human trials demonstrated correlation between vector metrics and cardiac pressure measurements indicative of contractility. Specifically, the ENSITE® NAVX® system was used to determine real-time positions of indwelling electrodes in the heart. The acquired position information for RV and LV electrodes and a defined RV-to-LV vector was then analyzed. The analysis demonstrated that an RV electrode could be used as a base of a vector and that an LV electrode could be used as a tip of a vector where the resulting RV-to-LV vector rotated and varied in magnitude with respect to time during a cardiac cycle. Vector rotational angle and vector magnitude were compared to chamber pressure, which, when plotted, demonstrated how these vector metrics can serve as indicators of cardiac mechanics. Such an exemplary method provides, in real-time, an hemodynamic index to pick a best pacing location and device configuration during implantation without necessarily requiring an interpretation of complex 3-D patterns of wall movement.

As described in more detail below, the trials demonstrated that as the heart contracts, a defined RV-to-LV vector rotates in a counter-clockwise direction during a systolic phase of a cardiac cycle and in a clockwise direction during a diastolic phase of a cardiac cycle. The trials demonstrated that, at the end of systole, RV-to-LV vector length is at its minimum and its angle from the start of pacing is at or near its maximum.

Trials demonstrated that vector "waveforms" for magnitude and angle were repeatable for paced beats. Based on the trials, it was observed that when vector angle reached its maximum, vector magnitude was at or near its minimum, representing the farthest extent of contraction and rotation of the heart. In practice, if such a correlation is not achieved (e.g., due to an inherent delay), as described herein, it is still possible to use only magnitude waveform and ECG to determine RV-to-LV vector amplitude. By extension, if the time of peak angular rotation does not align with the time of peak-minimum distance, this indicates some dissociation of myocardial shortening from twist, indicative of pathologic dyssynchrony. The vector analysis from animal and human data showed that above observation was consistent. An analysis of trial data also demonstrated a strong correlation between vector magnitude and (i) chamber pressure gradient (dP/dt), (ii) ventricular dyssynchrony (e.g., RV-LV) and (iii) temporal dispersion time. Hence, the vector magnitude metric can be used as an indicator of cardiac performance.

Various exemplary methods can include measuring an electrode-to-electrode vector distance (e.g., RV-to-LV vector or other configuration such as RA-to-RV vector, RA-to-LV vector) over multiple cardiac cycles and analyzing the vector distance to determine an optimal pacing configuration, for example, by identifying a best location for fixation of an electrode-bearing pacing lead. For two vectors (e.g., a reference vector "A" and a test vector "B"), the dot product $(A \cdot B = |A||B|\cos\theta)$ can also give the rotational angle and angular velocity or acceleration, which may be used to assess degree of angular contraction. In such an example, a reference vector may be defined based on measurement of positions at delivery time of a pacing stimulus (e.g., V-pulse) or at time of detection of an R-wave for a spontaneous or intrinsic activation of the heart.

In the trials described herein, the ENSITE® NAVX® system is programmed to calculate vector metrics (e.g., magnitude and angle) in real-time. For example, during an intraoperative procedure (i.e., acute procedure), a clinician may choose to:

(i) investigate different lead locations for pacing schemes such as BiV, LV-only, RV-only (e.g., various electrode combinations of tip/ring electrodes or LV1/LV2/LV3 electrodes of a quad-polar LV lead);

(ii) investigate configurations for different LV coronary circumflex branches;

(iii) investigate configurations for different LV distal distance;

(iv) investigate different epicardial positions for an LV lead (e.g., by subxiphoid access to the intrapericardial space);

(v) investigate different interatrial, intraatrial, atrioventricular, interventricular, and intraventricular delays.

During a chosen maneuver or after a chosen maneuver is completed, a computing device such as a programmed localization system can output one or more recommendations based, for example, on maximum contraction and maximum angular displacement. As described herein, an exemplary method may determine angular acceleration and contractile velocity, which are time derivatives of aforementioned vector magnitude waveforms and vector angle waveforms.

An exemplary method can include calculating (i) contractility index by a change in vector amplitude (e.g., $\Delta$ in vector amplitude such as difference between a minimum and maximum over a cardiac cycle); (ii) maximum positive slope from a vector magnitude waveform; (iii) angular or rotational changes of vectors; and/or (iv) changes in angle between two vectors (e.g., for AV or VD VV optimization using vectors such as a RV-to-RA vector, a LV-to-RA vector, etc.).

An exemplary method can optionally analyze position information for multiple RV-to-LV vectors. For example, with a quadpolar or other multi-polar LV lead, and/or with a multipolar lead or mapping catheter in the RV, a series of RV-to-LV vectors (or LV-to-RV vectors) can be computed (e.g., at each "level" of electrode). Where information exists for multiple vectors, metrics such as differential twist with respect to long-axis position (analog of torsion in the engineering sense) can be computed. In such a method, a longitudinal dispersion of time-to-peak-twist can be minimized to produce maximum torsional synchrony. Alternatively, an optimization process may consider an amount of segmental twist or torsion to be made more uniform, for example, to result in a reduction of adverse remodeling.

As described herein, various leads and electrodes can be used to generate vectors whose magnitude and angle can be analyzed. For example, a vector from RA-to-RV electrodes, or RA-to-LV electrodes, or $CS_{proximal}$-to-$LV_{distal}$ electrodes can be used as a surrogate for long axis shortening (magnitude) and apex-to-base rotation (angle).

As described herein, various exemplary techniques can be used to make decisions as to cardiac pacing therapy and optimization of a cardiac pacing therapy (e.g., CRT or other pacing therapies). In a clinical trial, acute resynchronization was shown to be a significant factor in assessing CRT efficacy and long-term outcome[1]. Various methods described herein, build on this clinical finding by formulating specialized techniques and metrics associated with locations for pacing, sensing or pacing and sensing. In turn, a clinician can assess how a particular CRT therapy or configuration thereof may be expected to perform at time of implant or, in some instances, after implant.

[1] GB Bleeker, SA Mollema, ER Holman, N Van De Veire, C Ypenburg, E Boersma, EE van der Wall, MJ Schalij, JJ Bax. "Left Ventricular Resynchronization is Mandatory for Response to Cardiac Resynchronization Therapy: Analysis in Patients with Echocardiographic Evidence of Left Ventricular Dyssynchrony at Baseline". *Circulation* 2007; 116: 1440-1448.

An exemplary stimulation device is described followed by various techniques for acquiring and calculating metrics. The drawings and detailed description elucidate details of various distinct stability metrics that may be used singly or in combination during an assessment or an optimization process (e.g., acute or chronic).

Exemplary Stimulation Device

The techniques described below are intended to be implemented in connection with any stimulation device that is configured or configurable to delivery cardiac therapy and/or sense information germane to cardiac therapy.

FIG. 1 shows an exemplary stimulation device 100 in electrical communication with a patient's heart 102 by way of three leads (a right atrial lead 104, a left ventricular lead 106 and a right ventricular lead 108), suitable for delivering multi-chamber stimulation and shock therapy. The leads 104, 106, 108 are optionally configurable for delivery of stimulation pulses suitable for stimulation of nerves or other tissue. In addition, in the example of FIG. 1, the device 100 includes a fourth lead 110 having multiple electrodes 144, 144', 144" suitable for stimulation of tissue and/or sensing of physiologic signals. This lead may be positioned in and/or near a patient's heart and/or remote from the heart.

FIG. 1 also shows approximate locations of the right and left phrenic nerves 154, 158. The phrenic nerve is made up mostly of motor nerve fibers for producing contractions of the diaphragm. In addition, it provides sensory innervation for various components of the mediastinum and pleura, as well as the upper abdomen (e.g., liver and gall bladder). The right phrenic nerve 154 passes over the brachiocephalic artery, posterior to the subclavian vein, and then crosses the root of the right lung anteriorly and then leaves the thorax by passing through the vena cava hiatus opening in the diaphragm at the level of T8. More specifically, with respect to the heart, the right phrenic nerve 154 passes over the right atrium while the left phrenic nerve 158 passes over the pericardium of the left ventricle and pierces the diaphragm separately. While certain therapies may call for phrenic nerve stimulation (e.g., for treatment of sleep apnea), in general, cardiac pacing therapies avoid phrenic nerve stimulation through judicious lead and electrode placement, selection of electrode configurations, adjustment of pacing parameters, etc.

Referring again to the various leads of the device 100, the right atrial lead 104, as the name implies, is positioned in and/or passes through a patient's right atrium. The right atrial lead 104 is configured to sense atrial cardiac signals and/or to provide right atrial chamber stimulation therapy. As described further below, the right atrial lead 104 may be used by the device 100 to acquire far-field ventricular signal data. As shown in FIG. 1, the right atrial lead 104 includes an atrial tip electrode 120, which typically is implanted in the patient's right atrial appendage, and an atrial ring electrode 121. The right atrial lead 104 may have electrodes other than the tip 120 and ring 121 electrodes. Further, the right atrial lead 104 may include electrodes suitable for stimulation and/or sensing located on a branch.

To sense atrial cardiac signals, ventricular cardiac signals and/or to provide chamber pacing therapy, particularly on the left side of a patient's heart, the stimulation device 100 is coupled to the left ventricular lead 106, which in FIG. 1 is also referred to as a coronary sinus lead as it is designed for placement in the coronary sinus and/or tributary veins of the coronary sinus. As shown in FIG. 1, the coronary sinus lead 106 is configured to position at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

In the example of FIG. 1, the coronary sinus lead 106 includes a series of electrodes 123. In particular, a series of four electrodes are shown positioned in an anterior vein of the heart 102. Other coronary sinus leads may include a different number of electrodes than the lead 106. As described herein, an exemplary method selects one or more electrodes (e.g., from electrodes 123 of the lead 106) and determines characteristics associated with conduction and/or timing in the heart to aid in ventricular pacing therapy and/or assessment of cardiac condition. As described in more detail below, an illustrative method acquires information using various electrode configurations where an electrode configuration typically includes at least one electrode of a coronary sinus lead or other type of left ventricular lead. Such information may be used to determine a suitable electrode configuration for the lead 106 (e.g., selection of one or more electrodes 123 of the lead 106).

In the example of FIG. 1, as connected to the device 100, the coronary sinus lead 106 is configured for acquisition of ventricular cardiac signals (and optionally atrial signals) and to deliver left ventricular pacing therapy using, for example, at least one of the electrodes 123 and/or the tip electrode 122. The lead 106 optionally allows for left atrial pacing therapy, for example, using at least the left atrial ring electrode 124. The lead 106 optionally allows for shocking therapy, for example, using at least the left atrial coil electrode 126. For a complete description of a particular coronary sinus lead, the reader is directed to U.S. Pat. No. 5,466,254, "Coronary Sinus Lead with Atrial Sensing Capability" (Helland), which is incorporated herein by reference.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108, as connected to the device 100, is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead. A right ventricular lead may include a series of electrodes, such as the series 123 of the left ventricular lead 106.

FIG. 1 also shows a lead 160 as including several electrode arrays 163. In the example of FIG. 1, each electrode array 163 of the lead 160 includes a series of electrodes 162 with an associated circuit 168. Conductors 164 provide an electrical supply and return for the circuit 168. The circuit 168 includes control logic sufficient to electrically connect the conductors 164 to one or more of the electrodes of the series 162. In the example of FIG. 1, the lead 160 includes a lumen 166 suitable for receipt of a guidewire to facilitate placement of the lead 160. As described herein, any of the leads 104, 106, 108 or 110 may include one or more electrode array, optionally configured as the electrode array 163 of the lead 160.

Figure 2:
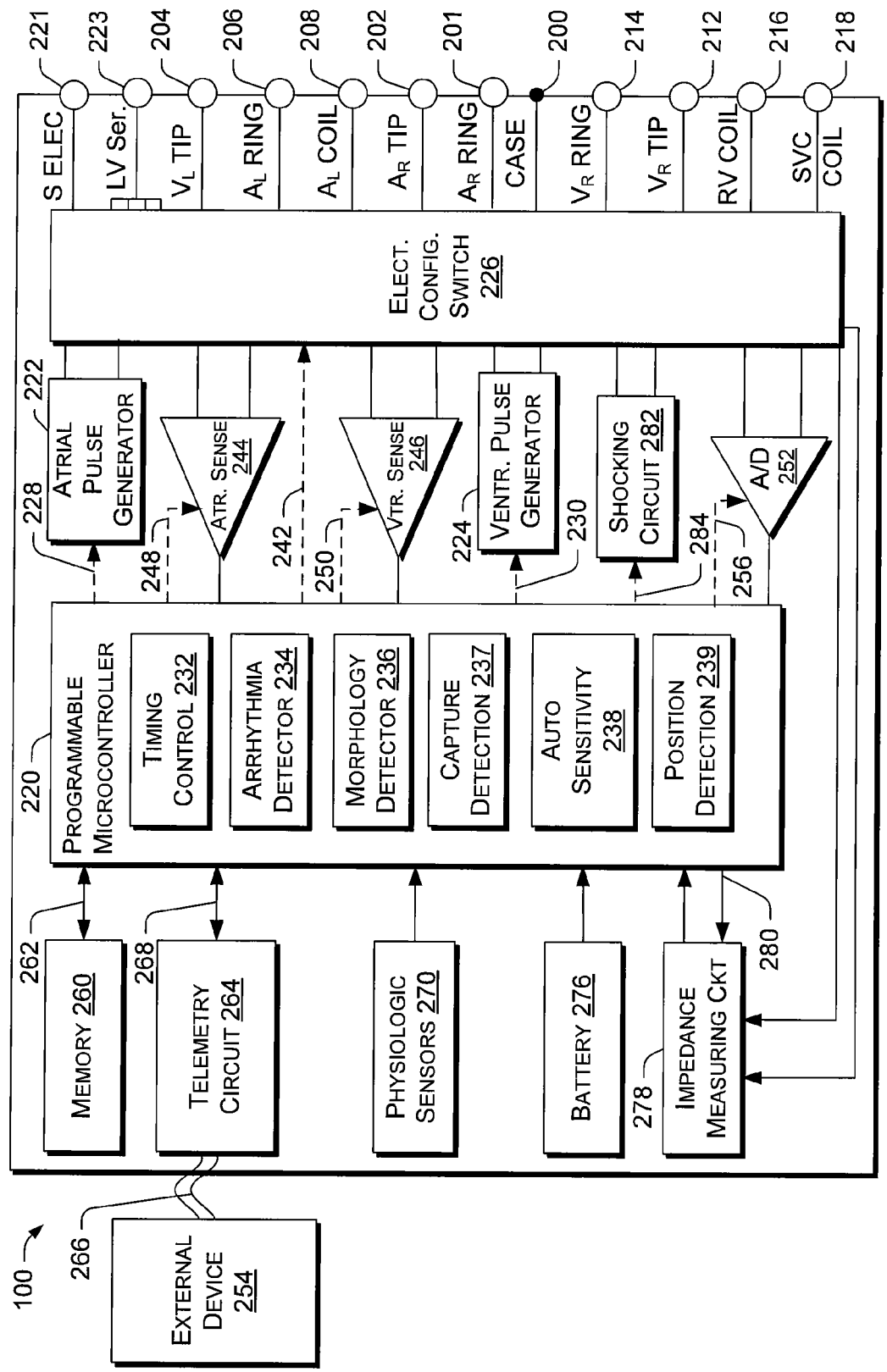
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of the device 100. The device 100 can be capable of treating both fast and slow arrhythmias with stimulation therapy, including cardioversion, defibrillation, and pacing stimulation. While a particular multi-chamber device is shown, it is to be appreciated and understood that this is for illustration purposes only. Thus, the techniques, methods, etc., described below can be implemented in connection with any suitably configured or configurable device. Accordingly, one of skill in the art could readily duplicate, eliminate, or disable the appropriate circuitry in any desired combination to provide a device capable of treating the appropriate chamber(s) or regions of a patient's heart.

Housing 200 for the device 100 is often referred to as the "can", "case" or "case electrode", and may be programmably selected to act as the return electrode for all "unipolar" modes. As described below, various exemplary techniques implement unipolar sensing for data that may include indicia of functional conduction block in myocardial tissue. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221, 223 (shown schematically and, for convenience, the names of the electrodes to which they are connected are shown next to the terminals).

To achieve right atrial sensing, pacing and/or other tissue sensing, stimulation, etc., the connector includes at least a right atrial tip terminal ($A_R$ TIP) 202 adapted for connection to the right atrial tip electrode 120. A right atrial ring terminal ($A_R$ RING) 201 is also shown, which is adapted for connection to the right atrial ring electrode 121. To achieve left chamber sensing, pacing, shocking, and/or other tissue sensing, stimulation, etc., the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing. For example, electrodes of the lead 110 may connect to the device 100 at the terminal 221 or optionally at one or more other terminals.

A terminal 223 allows for connection of a series of left ventricular electrodes. For example, the series of four electrodes 123 of the lead 106 may connect to the device 100 via the terminal 223. The terminal 223 and an electrode configuration switch 226 allow for selection of one or more of the series of electrodes and hence electrode configuration. In the example of FIG. 2, the terminal 223 includes four branches to the switch 226 where each branch corresponds to one of the four electrodes 123.

To support right chamber sensing, pacing, shocking, and/or other tissue sensing, stimulation, etc., the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052, the state-machine of U.S. Pat. Nos. 4,712,555 and 4,944,298, all of which are incorporated by reference herein. For a more detailed description of the various timing intervals used within the stimulation device and their inter-relationship, see U.S. Pat. No. 4,788,980, also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

The microcontroller 220 further includes timing control circuitry 232 to control the timing of the stimulation pulses (e.g., pacing rate, atrio-ventricular (AV) delay, interatrial conduction (AA) delay, or interventricular conduction (VV) delay, etc.) as well as to keep track of the timing of refractory periods, blanking intervals, noise detection windows, evoked response windows, alert intervals, marker channel timing, etc., which is well known in the art.

The microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The microcontroller 220 further includes an optional position and/or metrics module 239. The module 239 may be used for purposes of acquiring position information, for example, in conjunction with a device (internal or external) that may use body surface patches or other electrodes (internal or external). The microcontroller 220 may initiate one or more algorithms of the module 239 in response to a signal detected by various circuitry or information received via the telemetry circuit 264. Instructions of the module 239 may cause the device 100 to measure potentials using one or more electrode configurations where the potentials correspond to a potential field generated by current delivered to the body using, for example, surface patch electrodes. Such a module may help monitor electrode positions and cardiac mechanics in relationship to cardiac electrical activity and may help to optimize cardiac resynchronization therapy. The module 239 may include instructions for vector analyses, for example, based on locally acquired or transmitted position information. The module 239 may operate in conjunction with various other modules and/or circuits of the device 100 (e.g., the impedance measuring circuit 278, the switch 226, the A/D 252, etc.).

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial and ventricular sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each of the sensing circuits 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation) and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Cardiac signals are also applied to inputs of an analog-to-digital (A/D) data acquisition system 252. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or another lead (e.g., the lead 110) through the switch 226 to sample cardiac signals or other signals across any pair or other number of desired electrodes. A control signal 256 from the microcontroller 220 may instruct the ND 252 to operate in a particular mode (e.g., resolution, amplification, etc.).

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming and operation of the device 100.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation," to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, VV Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, oxygen concentration of blood, pH of blood, $CO_2$ concentration of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 which is hereby incorporated by reference.

The one or more physiologic sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As already mentioned, the implantable device 100 includes impedance measurement circuitry 278. Such a circuit may measure impedance or electrical resistance through use of various techniques. For example, the device 100 may deliver a low voltage (e.g., about 10 mV to about 20 mV) of alternating current between the RV tip electrode 128 and the case electrode 200. During delivery of this energy, the device 100 may measure resistance between these two electrodes where the resistance depends on any of a variety of factors. For example, the resistance may vary inversely with respect to volume of blood along the path.

In another example, resistance measurement occurs through use of a four terminal or electrode technique. For example, the exemplary device 100 may deliver an alternating current between one of the RV tip electrode 128 and the case electrode 200. During delivery, the device 100 may measure a potential between the RA ring electrode 121 and the RV ring electrode 130 where the potential is proportional to the resistance between the selected potential measurement electrodes.

With respect to two terminal or electrode techniques, where two electrodes are used to introduce current and the same two electrodes are used to measure potential, parasitic electrode-electrolyte impedances can introduce noise, especially at low current frequencies; thus, a greater number of terminals or electrodes may be used. For example, aforementioned four electrode techniques, where one electrode pair introduces current and another electrode pair measures potential, can cancel noise due to electrode-electrolyte interface impedance. Alternatively, where suitable or desirable, a two terminal or electrode technique may use larger electrode areas (e.g., even exceeding about 1 $cm^2$) and/or higher current frequencies (e.g., above about 10 kHz) to reduce noise.

Figure 3:
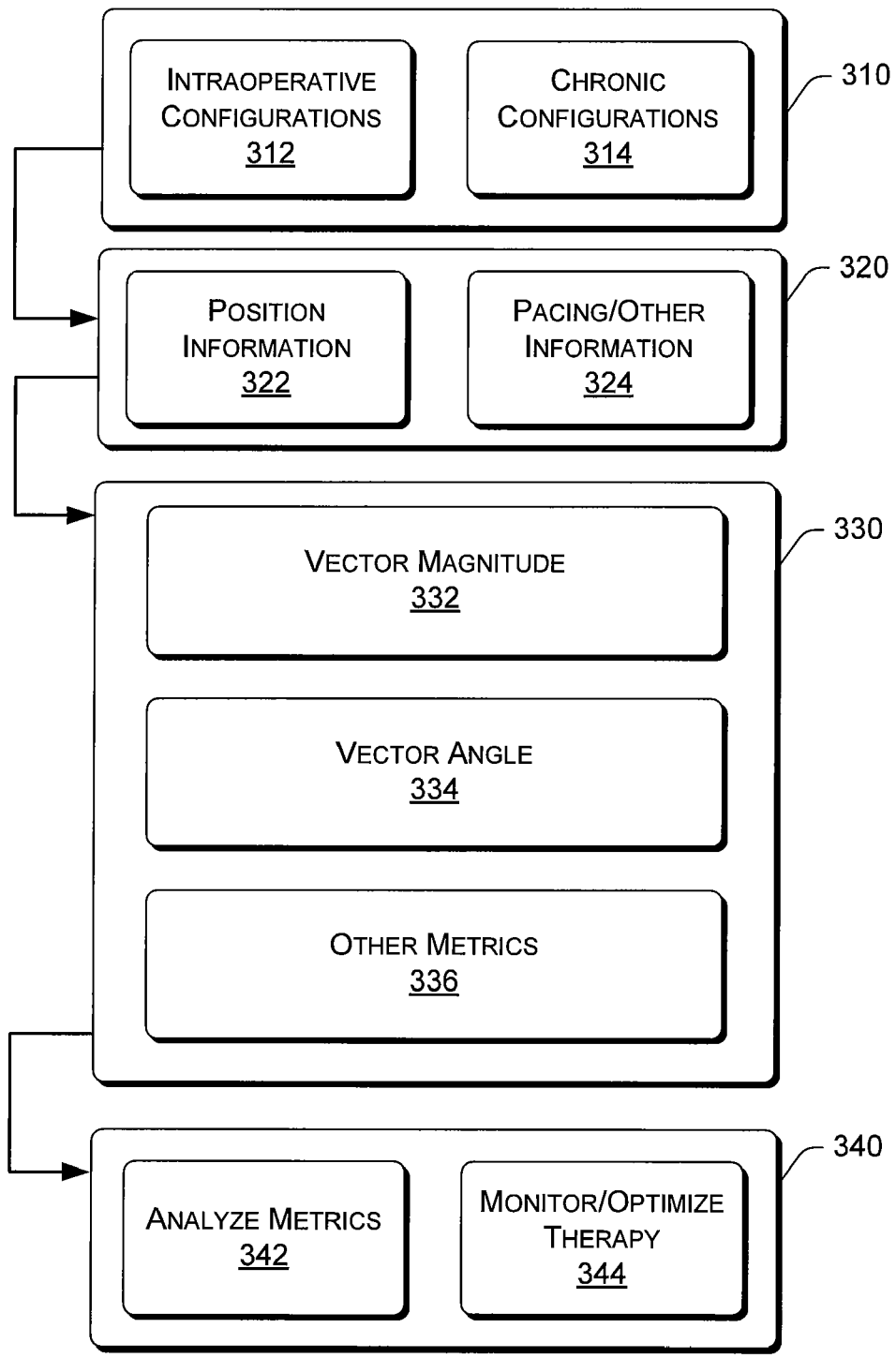
FIG. 3 is a block diagram of an exemplary method for selecting one or more configurations, optimizing therapy and/or monitoring conditions based at least in part on one or more vector metrics.

FIG. 3 shows an exemplary method 300 for acquiring position information and calculating one or more metrics 330. In the example of FIG. 3, the method 300 includes a configurations block 310 that includes intraoperative configurations 312 and chronic configurations 314. The intraoperative configurations 312 pertain to configurations that may be achieved during an operative procedure. For example, during an operative procedure, one or more leads (and/or catheter(s)) may be positioned in a patient where the one or more leads are connected to, or variously connectable to, a device configured to acquire information and optionally to deliver electrical energy to the patient (e.g., to the heart, to a nerve, to other tissue, etc.). The chronic configurations 314 pertain to configurations achievable by a chronically implanted device and its associated lead or leads. In general, intraoperative configurations include those achievable by physically re-positioning a lead (or catheter) in a patient's body while chronic configurations normally do not allow for re-positioning as a lead or leads are usually anchored during implantation or become anchored in the weeks to months after implantation. Chronic configurations do, however, include selection of a subset of the multiple implanted electrodes, for example using the tip electrode versus the first ring electrode as a cathode or using the tip and first ring as a bipolar pair versus using the tip and ring as two independent cathodes. Thus, intraoperative configurations include configurations available by changing device settings, electrode selection, and physical position of electrodes, while chronic configurations include only those configurations available by changing device settings and electrode selection, or "electronic repositioning" of one or more stimulation electrodes.

As indicated in FIG. 3, an acquisition block 320 includes acquisition of position information 322 and optionally acquisition of pacing and/or other information 324 (e.g., electrical information as to electrical activity of the heart, biosensor information, etc.). While an arrow indicates that a relationship or relationships may exist between the configurations block 310 and the acquisition block 320, acquisition of information may occur by using in part an electrode (or other equipment) that is not part of a configuration. For example, the acquisition block 320 may rely on one or more surface electrodes that define a coordinate system or location system for locating an electrode that defines one or more configurations. For example, three pairs of surface electrodes positioned on a patient may be configured to deliver current and define a three-dimensional space whereby measurement of a potential locates an electrode in the three-dimensional space.

As described herein, an electrode may be configured for delivery of energy to the body; for acquisition of electrical information; for acquisition of position information; for acquisition of electrical information and position information; for delivery of energy to the body and for acquisition of electrical information; for delivery of energy to the body and for acquisition of position information; for delivery of energy to the body, for acquisition of electrical information and for acquisition of position information.

In various examples, acquisition of position information occurs by measuring one or more potentials where the measuring relies on an electrode that assists in determining a position of the electrode or other item (e.g., a lead or sensor) where the electrode may also be configured to sense signals and/or deliver energy to the body (e.g., electrical energy to pace a chamber of the heart). For example, an electrode may deliver energy sufficient to stimulate the heart and then be tracked along one or more dimensions to monitor the position information resulting from the stimulation. Further, such an electrode may be used to acquire electrical information (e.g., an IEGM that evidences an evoked response). Such an electrode can perform all three of these tasks with proper circuitry and control. For example, after delivery of the energy, the electrode may be configured for acquiring one or more potentials related to position and for acquiring an electrogram. To acquire potentials and an electrogram, circuitry may include gating or other sampling techniques (e.g., to avoid circuitry or interference issues). Such circuitry may rely on one sampling frequency for acquiring potentials for motion tracking and another sampling frequency for acquiring an electrogram.

The method 300 of FIG. 3 includes a metrics block 330 that includes vector magnitude 332, vector angle 334 and other metrics 336. Such metrics are based, at least in part, on acquired position information. As described herein, a vector may be defined between two electrodes and may be referenced with respect to one or more other electrodes. For example, a triangle may be defined between a right atrial electrode, a right ventricular electrode and an electrode in a vein of a lateral wall of the left ventricle. An analysis of position of these electrodes with respect to time may indicate that two of the electrodes exhibit less movement over a cardiac cycle when compared to a third electrode. In such a scenario, the two electrodes that exhibit less movement may be used as a reference or references to more accurately track a vector with its vector tip defined by the position of third electrode. As described herein, trials demonstrate that an electrode located in the apex of the right ventricle moves less than an electrode located along the lateral wall of the left ventricle (e.g., in a tributary vein of the coronary sinus). In trials, various aspects of a vector defined by an electrode located in right ventricular apex to an electrode located in a vein of the lateral wall of the left ventricle were analyzed with respect to indicators of cardiac performance. The results demonstrate that such a RV-to-LV vector can be used as an indicator of cardiac performance.

In the example of FIG. 3, the conclusion block 340 may perform actions such as to analyze metrics 342 and/or to optimize or monitor patient and/or device condition 344 based on one or more of the metrics 330. These options are described in more detail with respect to FIG. 4.

Figure 4:
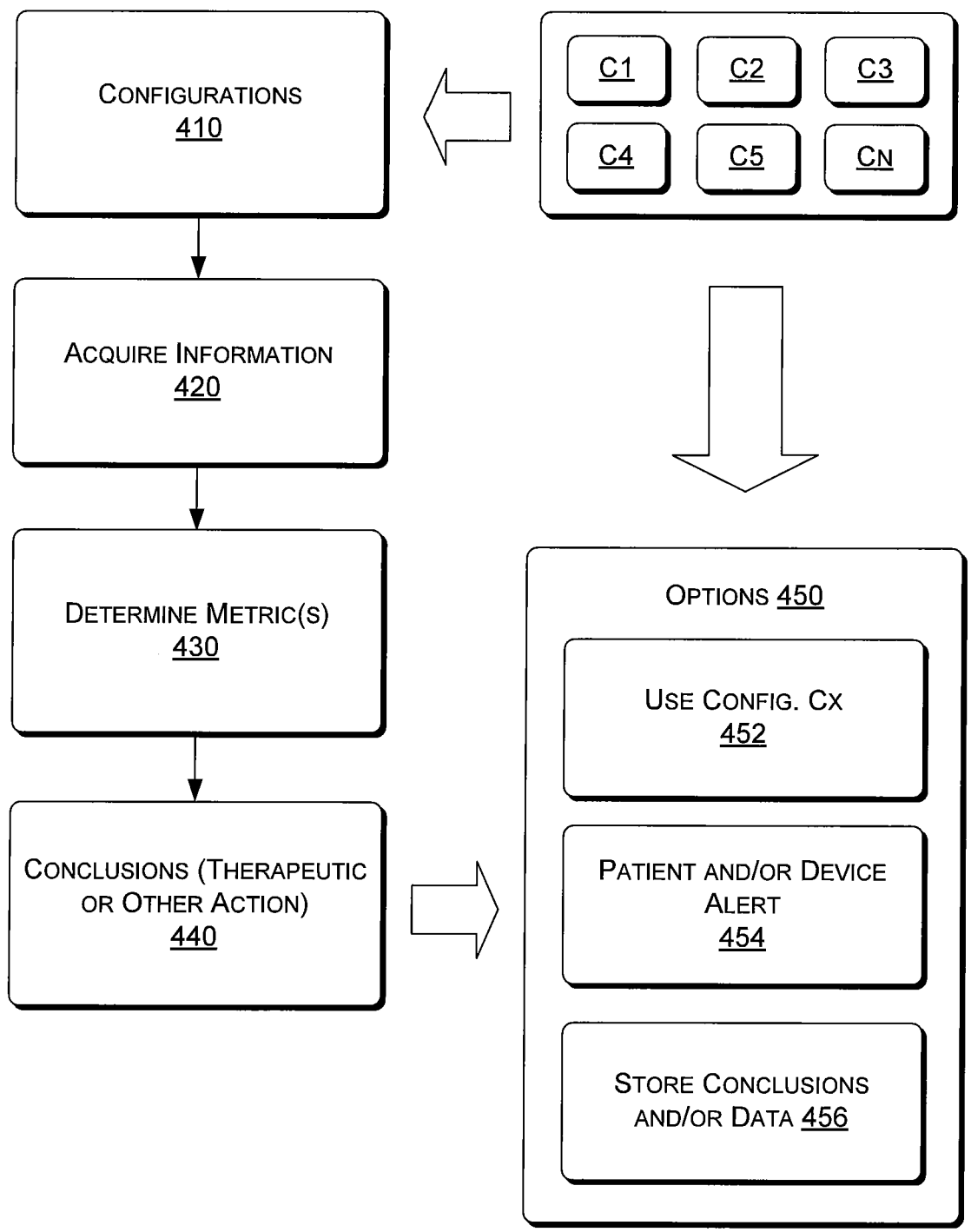
FIG. 4 is a block diagram of the exemplary method of FIG. 3 along with various options.

FIG. 4 shows an exemplary method 400 with various configurations 410 (C1, C2, . . . , Cn) and options 450. As mentioned, a configuration may be defined based on factors such as electrode location (e.g., with respect to some physiological feature of the heart or another electrode), stimulation parameters for an electrode or electrodes and, where appropriate, one or more interelectrode timings. Hence, with reference to FIG. 1, C1 may be a configuration that relies on the RV tip electrode 128, the RV ring electrode 130, the LV tip electrode 122 and the LV ring electrode 124 while C2 may be a configuration that relies on the same electrodes as C1 but where the stimulation polarity for the LV electrodes is reversed. Further, C3 may rely on the same electrodes where the timing between delivery of a stimulus to the RV and delivery of a stimulus to the LV is different compared to C1. Yet further, C4 may rely on the same electrodes where the duration of a stimulus to the RV is different compared to C1. In these foregoing examples, configurations provide for one or more electrodes to deliver energy to stimulate the right ventricle and for one or more electrodes to deliver energy to stimulate the left ventricle. In other examples, configurations may provide for stimulation of a single chamber at one or more sites, stimulation of one chamber at a single site and another chamber at multiple sites, multiple chambers at multiple sites per chamber, etc.

As mentioned, configurations can include one or more so-called "stimulators" and/or "sensors". Thus, the configurations block 410 may select a configuration that includes one or more of an electrode, a lead, a catheter, a device, etc. In various examples, a stimulator or a sensor can include one or more electrodes configured to measure a potential or potentials to thereby directly or indirectly provide position information for the stimulator or the sensor. For example, a lead-based oximeter (oxygen sensor) may include an electrode configured to measure a potential for providing position information for the oximeter or a lead-based RF applicator may include electrodes configured to measure potentials for providing position information for the RF applicator or a tip of the lead.

In an acquisition block 420, acquisition occurs for information where such information includes position information that pertains to one or more electrodes of a configuration. In a determination block 430, one or more metrics are determined based at least in part on the acquired information (see, e.g., the metrics block 330 of FIG. 3). A conclusions block 430 provides for therapeutic or other action, which may be selected from one or more options 450.

In the example of FIG. 4, the one or more options 450 include selection of a configuration 452 (e.g., Cx, where x is a number selected from 1 to n), issuance of a patient and/or device alert 454 that pertains to condition of a patient or a condition of a device or associated lead(s) or electrode(s), and storage of conclusion(s) and/or data 456. The options 450 may be associated with the configurations 410, as indicated by an arrow. For example, storage of conclusions and/or data 456 may also store specific configurations, a generalization of the configurations (e.g., one or more shared characteristics), a device/system arrangement (e.g., where the number and types of configurations would be known based on the arrangement), etc.

As described herein, an exemplary method can include: locating one or more electrodes within the heart and/or surrounding space (e.g., intra-chamber, intra-vascular, intraperi-cardial, etc., which may be collectively referred to as "cardiac space"); acquiring information (e.g., via one or more measured potentials using a localization system such as the ENSITE® NAVX® system or other system with appropriate features); and calculating one or more metrics for at least one of the one or more electrodes. In such a method, the located electrodes may be configured for acquisition of electrical information indicative of physiological function (e.g., IEGMs, muscle signals, nerve signals, etc.). Further, with respect to acquisition of information, an acquisition system may operate at an appropriate sampling rate. For example, an acquisition system for position information may operate at a sampling rate of about 100 Hz (e.g., the ENSITE® NAVX® system can sample at about 93 Hz) and an acquisition system for electrical information may operate at a sampling rate of about 1200 Hz (e.g., in unipolar, bipolar or other polar arrangement).

An exemplary method may include preparing a patient for both implant of a device such as the device 100 of FIGS. 1 and 2 and for electroanatomic mapping study. Such preparation may occur in a relatively standard manner for implant prep, and using the ENSITE® NAVX® system or other similar technology for the mapping prep. As described herein, any of a variety of electroanatomic mapping or locating systems that can locate indwelling electrodes in and around the heart may be used.

Once prepped, a clinician or robot may place leads and/or catheters in the patient's body, including any leads to be chronically implanted as part of a therapy system (e.g., CRT), as well as optional additional electrodes that may yield additional information (e.g., to increase accuracy by providing global information or other information).

After an initial placement of an electrode-bearing catheter or an electrode-bearing lead, a clinician may then connect one or more electrodes to an electroanatomic mapping or localization system. The term "connection" can refer to physical electrical connection or wireless connection (e.g., telemetric, RF, ultrasound, etc.) with the electrodes or wireless connection with another device that is in electrical contact with the electrodes.

Once an appropriate connection or connections have been made, real-time position data for one or more electrodes may be acquired for various configurations or conditions. For example, position data may be acquired during normal sinus rhythm; pacing in one or more chambers; advancing, withdrawing, or moving a location of an electrode; pacing one or more different electrode configurations (e.g. multisite pacing); or varying inter-stimulus timing (e.g. AV delay, VV delay).

In various examples, simultaneous to the position recording, an intracardiac electrogram (IEGM) from each electrode can also be recorded and associated with the anatomic position of the electrode. While various examples refer to simultaneous acquisition, acquisition of electrical information and acquisition of position information may occur sequentially (e.g., alternate cardiac cycles) or interleaved (e.g., both acquired during the same cardiac cycle but offset by sampling time or sampling frequency).

In various exemplary methods, electrodes within the cardiac space may be optionally positioned at various locations (e.g., by continuous movement or by discrete, sequential moves), with a localization system recording the real-time position information at each electrode position in a point-by-point manner. Such position data can by associated with a respective anatomic point from which it was collected. By moving the electrodes from point to point during an intervention, the position data from each location can be analyzed, optionally with respect to vector definitions, vector operations, etc., to provide one or more metrics.

As explained, an exemplary method can include mapping one or more metrics, optionally in conjunction with one or more configuration parameters. In turn, an algorithm or a clinician may select a configuration (e.g., electrode location, multisite arrangement, AV/VV timing, pacing voltage, etc.) that yielded the best value for cardiac performance and use the selected configuration as a chronic configuration for the CRT system. Such a chronic configuration may be optionally updated from time to time (e.g., during a follow-up visit, in a patient environment, etc., depending on specific capabilities of a system).

Various exemplary methods, using either a single metric or a combination of more than one metric, may automatically select a configuration, present an optimal configuration for acknowledgement by a clinician, or present various configurations to a clinician along with pros and cons of each configuration (e.g., in objective or subjective terms). Pros and cons may pertain to cardiac performance, patient comfort (e.g., pain, lack of pain, overall feeling, etc.), device performance, etc. As described herein, various decisions are based on one or more vector metrics.

An exemplary method may rely on certain equipment at time of implant or exploration and other equipment after implantation of a device to deliver a cardiac therapy. For example, during an intraoperative procedure, wireless communication may not be required; whereas, during a follow-up visit, measured potentials for position of chronically implanted electrodes (e.g., mechanical information) and of measured IEGMs using chronically implanted electrodes (e.g., electrical information) may be communicated wirelessly from an implanted device to an external device. With respect to optimization or assessment of a chronically implanted system, in general, electrode location will not be altered (e.g., except for dislocation or failure), but other parameters altered to result in an optimal configuration (e.g., single- or multi-site arrangement, polarity, stimulation energy, timing parameters, etc.).

As discussed herein, various exemplary techniques deliver current and measure potential where potential varies typically with respect to cardiac mechanics (e.g., due to motion). For example, electrodes for delivery of current may be placed at locations that do not vary significantly with respect to cardiac mechanics or other patient motion (e.g., breathing) while one or more electrodes for measuring potential may be placed at a location or locations that vary with respect to cardiac mechanics or other patient motion. Alternatively, electrodes for measuring potential may be placed at locations that do not vary significantly with respect to cardiac mechanics or other patient motion while one or more electrodes for delivery of current may be placed at a location or locations that vary with respect to cardiac mechanics or other patient motion. Various combinations of the foregoing arrangements are possible as well. Electrodes may be associated with a catheter or a lead. In some instances, an electrode may be a "stand-alone" electrode, such as a case electrode of an implantable device (see, e.g., the case electrode 200 of the device 100 of FIGS. 1 and 2).

Figure 5:
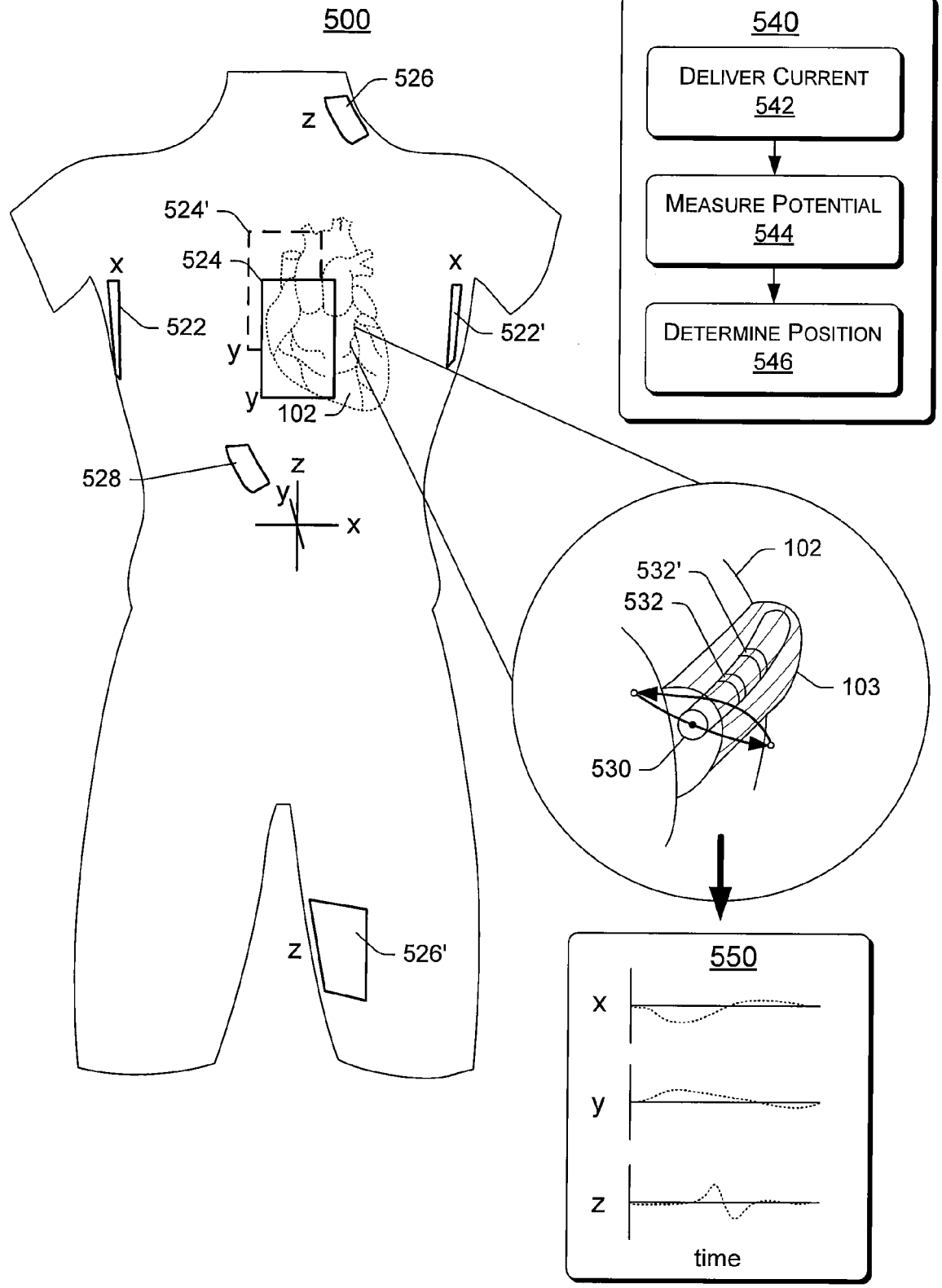
FIG. 5 is an exemplary arrangement of a lead and electrodes for acquiring position information and optionally other information for use in determining one or more vector metrics.

FIG. 5 shows an arrangement and method 500 that may rely in part on a commercially available system marketed as ENSITE® NAVX® navigation and visualization system (see also LOCALISA® system, Medtronic, Inc., Minnesota). The ENSITE® NAVX® system is a computerized storage and display system for use in electrophysiology studies of the human heart. The system consists of a console workstation, patient interface unit, and an electrophysiology mapping catheter and/or surface electrode kit. By visualizing the global activation pattern seen on color-coded isopotential maps in the system, in conjunction with the reconstructed electrograms, an electrophysiologist can identify the source of an arrhythmia and can navigate to a defined area for therapy. The ENSITE® system is also useful in treating patients with simpler arrhythmias by providing non-fluoroscopic navigation and visualization of conventional electrophysiology (EP) catheters.

As shown in FIG. 5, electrodes 532, 532', which may be part of a standard EP catheter 530 (or lead), sense electrical potential associated with current signals transmitted between three pairs of surface electrode patches 522, 522' (x-axis),

524, 524' (y-axis) and 526, 526' (z-axis). An addition electrode patch 528 (sometimes referred to as a "belly" patch) is available for reference, grounding or other function. The ENSITE® NAVX® System can also collect electrical data from a catheter and can plot a cardiac electrogram from a particular location (e.g., cardiac vein 103 of heart 102). Information acquired may be displayed as a 3-D isopotential map and as virtual electrograms. Repositioning of the catheter allows for plotting of cardiac electrograms from other locations. Multiple catheters may be used as well. A cardiac electrogram or electrocardiogram (ECG) of normal heart activity (e.g., polarization, depolarization, etc.) typically shows atrial depolarization as a "P wave", ventricular depolarization as an "R wave", or QRS complex, and repolarization as a "T wave". The ENSITE® NAVX® system may use electrical information to track or navigate movement and construct three-dimensional (3-D) models of a chamber of the heart.

A clinician can use the ENSITE® NAVX® system to create a 3-D model of a chamber in the heart for purposes of treating arrhythmia (e.g., treatment via tissue ablation). To create the 3-D model, the clinician applies surface patches to the body. The ENSITE® NAVX® system transmits an electrical signal between the patches and the system then senses the electrical signal using one or more catheters positioned in the body. The clinician may sweep a catheter with electrodes across a chamber of the heart to outline structure. Signals acquired during the sweep, associated with various positions, can then be used to generate a 3-D model. A display can display a diagram of heart morphology, which, in turn, may help guide an ablation catheter to a point for tissue ablation.

With respect to the foregoing discussion of current delivery and potential measurement, per a method 540, a system (e.g., such as the ENSITE® NAVX® system) delivers low level separable currents from the three substantially orthogonal electrode pairs (522, 522', 524, 524', 526, 526') positioned on the body surface (delivery block 542). The specific position of a catheter (or lead) electrode within a chamber of the heart can then be established based on three resulting potentials measured between the recording electrode with respect to a reference electrode, as seen over the distance from each patch set to the recording tip electrode (measurement block 544). Sequential positioning of a catheter (or lead) at multiple sites along the endocardial surface of a specific chamber can establish that chamber's geometry, i.e., position mapping (position/motion determination block 546). Where the catheter (or lead) 530 moves, the method 540 may also measure motion.

In addition to mapping at specific points, the ENSITE® NAVX® system provides for interpolation (mapping a smooth surface) onto which activation voltages and times can be registered. Around 50 points are required to establish a surface geometry and activation of a chamber at an appropriate resolution. The ENSITE® NAVX® system also permits the simultaneous display of multiple catheter electrode sites, and also reflects real-time motion of both ablation catheters and those positioned elsewhere in the heart.

The ENSITE® NAVX® system relies on catheters for temporary placement in the body. Various exemplary techniques described herein optionally use one or more electrodes for chronic implantation. Such electrodes may be associated with a lead, an implantable device, or other chronically implantable component. Referring again to FIG. 3, the configuration block 310 indicates that intraoperative configurations 312 and chronic configurations 314 may be available. Intraoperative configurations 312 may rely on a catheter and/or a lead suitable for chronic implantation.

With respect to motion (e.g., change in position with respect to time), the exemplary system and method 500 may track motion of an electrode in one or more dimensions. For example, a plot 550 of motion versus time for three dimensions corresponds to motion of one or more electrodes of the catheter (or lead) 530 positioned in a vessel 103 of the heart 102 where the catheter (or lead) 530 includes the one or more electrodes 532, 532'. Two arrows indicate possible motion of the catheter (or lead) 530 where hysteresis may occur over a cardiac cycle. For example, a systolic path may differ from a diastolic path. An exemplary method may analyze hysteresis for any of a variety of purposes including assessing stability of an electrode of a catheter (or lead), assessing stability of a catheter (or lead), selection of a stimulation site, selection of a sensing site, diagnosis of cardiac condition, etc.

The exemplary method 540, as mentioned, includes the delivery block 542 for delivery of current, the measurement block 544 to measure potential in a field defined by the delivered current and the determination block 546 to determine position or motion based at least in part on the measured potential. According to such a method, position or motion during systole and/or diastole may be associated with electrical information or other information (e.g., biosensor, loading of a catheter or lead, intrinsic/paced activation, etc.). Alone, or in combination with other information, the position or motion information may be used for various assessments (e.g., stability assessments), selection of optimal stimulation site(s), determination of hemodynamic surrogates (e.g., surrogates to stroke volume, contractility, etc.), optimization of CRT, placement of leads, determination of pacing parameters (AV delay, VV delay, etc.), etc.

The system 500 may use one or more features of the aforementioned ENSITE® NAVX® system. For example, one or more pairs of electrodes (522, 522', 524, 524', 526, 526' and optionally 528) may be used to define one or more dimensions by delivering an electrical signal or signals to a body and/or by sensing an electrical signal or signals. Such electrodes (e.g., patch electrodes) may be used in conjunction with one or more electrodes positioned in the body (e.g., the electrodes 532, 532').

The exemplary system 500 may be used to track position or motion of one or more electrodes due to systolic function, diastolic function, respiratory function, etc. Electrodes may be positioned along the endocardium and/or epicardium during a scouting or mapping process for use in conjunction with electrical information. Such information may also be used alone, or in conjunction with other information (e.g., electrical information), for assessing stability of an electrode or electrodes for use in delivering a therapy or for identifying the optimal location of an electrode or electrodes for use in delivering a therapy. For example, a location may be selected for optimal stability, for optimal stimulation, for optimal sensing, or for other purposes.

With respect to stimulation, stimulation may be delivered to control cardiac mechanics (e.g., contraction of a chamber of the heart) and position or motion information may be acquired where such information is associated with the controlled cardiac mechanics. An exemplary selection process may identify the best stimulation site based on factors such as electrical activity, electromechanical delay, extent of motion, synchronicity of motion where motion may be classified as motion due to systolic function or motion due to diastolic function. In general, motion information corresponds to motion of an electrode or electrodes (e.g., endocardial electrodes, epicardial electrodes, etc.) and may be related to motion of the heart or other physiology.

As described with respect to FIG. 5, a localization system can acquire position information for one or more electrodes on a lead or catheter. The ENSITE® NAVX® system can operate at a sampling frequency around 100 Hz (10 ms), which, for a cardiac rhythm of 60 bpm, allows for 100 samples per electrode per cardiac cycle. In various examples, sampling may be gated to occur over only a portion of a cardiac cycle. Gating may rely on fiducial markers such as peaks, gradients, crossings, etc., in an electrogram of heart activity. Other techniques for gating can include accelerometer techniques, impedance techniques, pressure techniques, flow techniques, etc. For example, an accelerometer signal slope above a threshold value (e.g., due to cardiac contraction or relaxation) can be used to commence acquisition of information or to terminate acquisition of information during a cardiac cycle. Such a technique may be repeated over multiple cardiac cycles with or without application of electrical stimuli, medication, body position changes, etc.

As described herein, for one or more electrodes, a localization system can provide four-dimensional information (e.g., x, y, z and time). The four-dimensional information describes a three-dimensional trajectory in space that can be analyzed or displayed in part, in whole or at one or more key points in time. As mentioned, various other types of information may be used to gate acquisition or to delineate points or segments of a trajectory. For example, information provided by a surface EKG, an intracardiac EGM, or other biosignal can delineate a point or event such as QRS onset or pacing pulse or a segment (e.g., QRS complex, QT interval, etc.).

Where an electrode is position in a vessel of the heart such as a vein (e.g., cardiac sinus (CS) vein or a tributary thereto), the trajectory of the electrode will follow cardiac motion of nearby myocardium. For example, a CS lead electrode will trace the path traversed by epicardium adjacent the CS or adjacent the particular CS tributary. If the lead position is stable in a branch, the trajectory for consecutive beats will typically remain within a bounded spatial volume; however, if the lead dislodges grossly, a shift in the CS lead electrode's position will be apparent in a display or analysis of the acquired information.

In various instances, depending on placement of electrodes that generate a localization field, respiration may affect accuracy of position data. For example, referring to FIG. 5, as a patient breathes, the torso changes shape, which can alter the alignment of the electrodes 522, 522', 524, 524', 526, 526' and 528. Further, as respiration introduces air into the body, dielectric properties of media between electrodes of a directional pair may change. To account for the affects of respiration, an exemplary data acquisition technique may include an algorithm that compensates for respiratory motion. Alternatively, compensation of filtering may be performed after data acquisition, for example, using one or more algorithms that identify frequencies in data that are likely related to respiration and adjust the data (e.g., filter or normalize) to compensate for respiration. In other instances, respiration gating may be used during data acquisition, for example, akin to techniques used during acquisition of nuclear magnetic resonance data (e.g., NMR or MRI data). For example, beats to be included in a stability index metric may be gated to a particular portion of the respiratory cycle.

The ENSITE® NAVX® system includes a so-called "RespComp" algorithm that uses a combination of impedance between various pairs of patches, which create the localization field, as a measure of respiratory motion. In yet another alternative, motion of electrodes that are known to be stable can be used to ascertain respiratory motion. For example, position data with respect to time may have low frequency content (approximately 0.1 Hz to approximately 0.5 Hz) that can be due to respiration, which can be subtracted from the motion of the electrode of which stability is of interest.

Instantaneous fluid status, among other variables, can cause some drift in position as measured by a localization system such as the ENSITE® NAVX® system. An exemplary method can include a correction factor that accounts for fluid status drift, which may be found by comparing position of a stable electrode from one cycle to the next and applying any measured offset to an electrode of interest.

As described herein, for various vector metrics, subtraction techniques or other techniques may act to reduce or eliminate fluid status contributions or movement contributions caused by respiration, the heart in the body (e.g., within a localization field) or by patient movement (e.g., change in posture, etc.).

Figure 6:
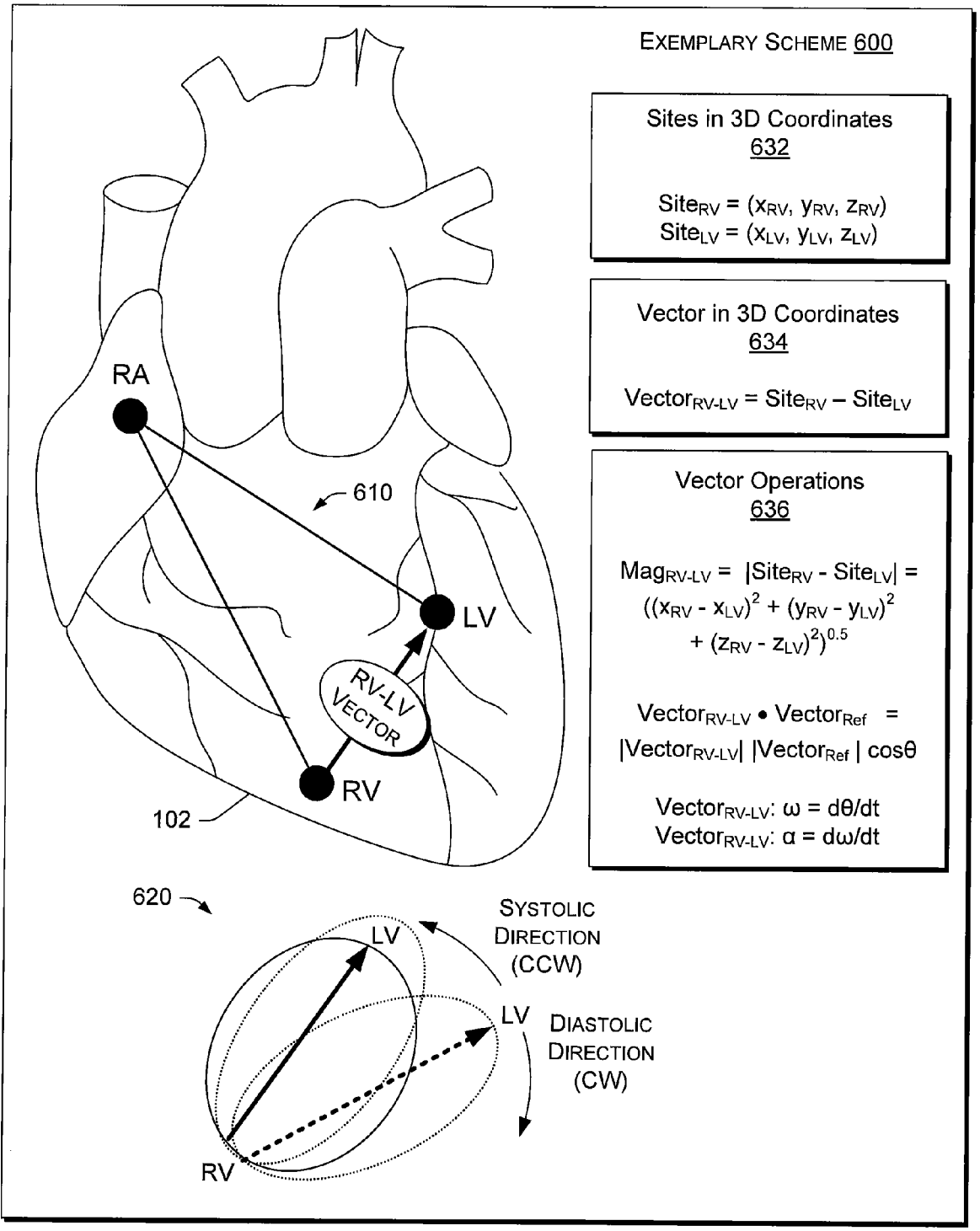
FIG. 6 is diagram of an exemplary scheme that tracks a vector that extends from a RV site to a LV site, referred to as a RV-to-LV vector.

FIG. 6 shows a diagram of an exemplary scheme 600 that relies on a RV-to-LV vector. In FIG. 6, a triangle 610 is shown with respect to the heart 102. The vertices of the triangle include a right atrial point (RA), a right ventricular point (RV) and a left ventricular point (LV). A diagram 620 illustrates movement of the RV-to-LV vector during a cardiac cycle. Specifically, when the heart 102 contracts, the vector from the RV point to the LV point rotates in a counter-clockwise direction during systole and rotates in clockwise direction during diastole. Trial data indicate that, at the end of systole, length of the RV-to-LV vector reaches a minimum while angle of rotation from delivery of a pacing stimulus (V-pulse) reaches a maximum. In the example of FIG. 6, the diagram 620 indicates that, during a cardiac cycle, motion of the RV point is much less than motion of the LV point. Further, data indicate that the RA point also tends to move much less than the LV point. Hence, length of the RA-to-RV segment of the triangle 610 varies less during a cardiac cycle than length of the RV-to-LV segment or the RA-to-LV segment. As described herein, by collecting data with respect to time, waveforms are generated that exhibit physiologic behavior. Such waveforms can be analyzed by one or more techniques where a result or results may be relied on for diagnosis, determining or selecting a configuration, etc.

As described herein, an exemplary method can include subtracting right ventricular position in a 3D coordinate system from left ventricular position in the 3D coordinate system, or vice versa, to remove from the analysis movement contributions caused by respiration, the heart itself or a combination of both respiration and the heart itself (e.g., movement of the heart in the body). Such a technique can also remove possible artifacts caused by body movements such as posture changes. In various scenarios, one or more subtraction techniques may be applied, for example, to isolate particular movement (e.g., consider a technique that subtracts contractile motion of a particular electrode). A centroid may also be calculated for various points (e.g., a centroid of a triangle defined by a RA electrode, a RV electrode and a LV electrode). In such an example, movement of the centroid may be tracked over time (e.g., as a centroid waveform) and analyzed to, for example, enhance diagnosis of cardiac condition or selection of a configuration (e.g., electrodes, timing parameters, etc.).

As shown in a block 632 of FIG. 6, for a site associated with the right ventricle, position of this site can be represented as $Site_{RV} = (x_{RV}, y_{RV}, z_{RV})$ and for a site associated with the left ventricle, position of this site can be represented as $Site_{LV} = (x_{LV}, y_{LV}, z_{LV})$. Given the foregoing notation, as shown in a block 634 of FIG. 6, a vector can be defined as $\text{Vector}_{RV-LV}=\text{Site}_{RV}-\text{Site}_{LV}$. As shown by the vector operations of a block 636 of FIG. 6, magnitude of this vector can be calculated as:

$$\text{Mag}_{RV-LV}=|\text{Site}_{RV}-\text{Site}_{LV}|=((x_{RV}-x_{LV})^2+(y_{RV}-y_{LV})^2+(z_{RV}-z_{LV})^2)^{0.5}$$

Also shown in the block 636, vector rotational angle can be calculated using the dot product of two vectors:

$$\text{Vector}_{RV-LV}\cdot\text{Vector}_{Ref}=|\text{Vector}_{RV-LV}||\text{Vector}_{Ref}|\cos\theta$$

In the foregoing equation, the arc cosine function provides the angle θ. As indicated in the block 636, angular velocity ω can be calculated from the time derivative of the angle (dθ/dt) and angular acceleration from the second time derivative of the angle (dω/dt). The various position data or angle data (or derivatives or other variants thereof), where available with respect to time, may be represented as waveforms. Such waveforms may be analyzed, for example, by comparing waveforms for different conditions (e.g., electrode configurations, stimulation parameters, patient positions, activity levels, etc.). Operations of the various blocks of the exemplary scheme 600 may be implemented as instructions for execution by a processor or processors and may be stored in a computer-readable medium, for example, associated with a computing device such as an implantable computing device or an external computing device.

The reference vector, $\text{Vector}_{Ref}$, is typically a fixed vector, for example, based on positions at a time of (or prior to) a ventricular stimulus (e.g., V-pacing) or an intrinsic ventricular event (e.g., R-sense) (e.g., to provide a baseline). As described herein, any time point or points may serve as a fiducial or fiducials in time, for example, with respect to the cardiac cycle. As explained with respect to FIG. 6, the vector RV-to-LV ($\text{Vector}_{RV-LV}$) is a changing vector that changes in response to contraction of the heart, whether caused by intrinsic activity or delivery of a stimulus (e.g., as associated with a pacing therapy).

Figure 7:
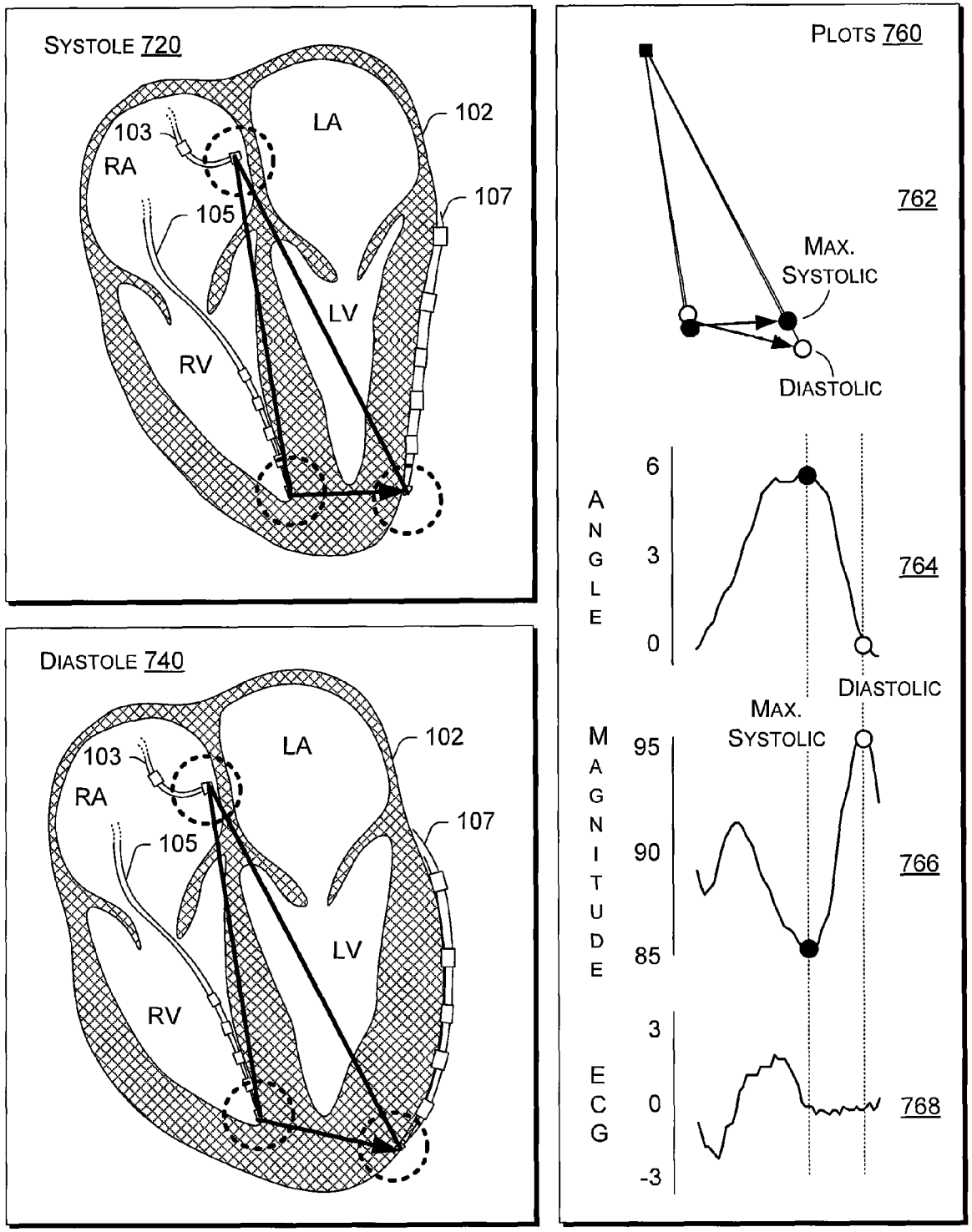
FIG. 7 is a diagram of a RA-RV-LV vector triangle and associated plots of a RV-to-LV vector with respect to a cardiac cycle.

FIG. 7 shows cross-sectional views of the heart during systole 720 and during diastole 740 along with various plots 760. The ventricles of the heart 102 are often referred to as having a diastolic phase (diastole) and a systolic phase (systole). During the diastolic phase blood fills the ventricles and during the systolic phase, blood is ejected from the heart. In the cross-sectional view of the heart corresponding to systole 720, the right ventricle and the left ventricle are shown as being of smaller area (and hence volume) than in the cross-sectional view of the heart corresponding to diastole 740.

The plots 760 include a plot of a triangle 762 with vertices corresponding to a right atrial electrode, a right ventricular electrode and an electrode along a lateral wall of the left ventricle. In the plot 762, a vector from the RV point to the LV point is shown for both maximum systolic contraction (filled circle) and maximum diastolic relaxation (open circle). In a vector angle plot 764 and a vector magnitude plot 766, filled circles identify angle and magnitude for a point in time of maximum systolic contraction while open circles identify angle and magnitude for a point in time of maximum diastolic relaxation. A surface ECG plot 768 is also shown, which indicates by its morphology that the data in the plots 764 and 766 corresponds to a paced cardiac cycle. The angle and magnitude of the plots 764 and 766 may be calculated according to the equations of the block 636 of FIG. 6. As indicated by the plots 764 and 766, angle and magnitude exhibit differing yet related morphologies for a cardiac cycle. As described herein, analysis of such metrics, optionally in association with other physiological information, can provide insight into cardiac mechanics and aid a clinician when setting-up an implantable device or programming an implantable device. Further, where such information is available chronically (post-implant), a clinician may monitor or adjust therapy. Where an implantable device includes circuitry to track magnitude, angle or magnitude and angle, such a device may be programmed to adjust therapy based on such metrics (e.g., adjusting one or more parameters associated with a therapy).

Figure 8:
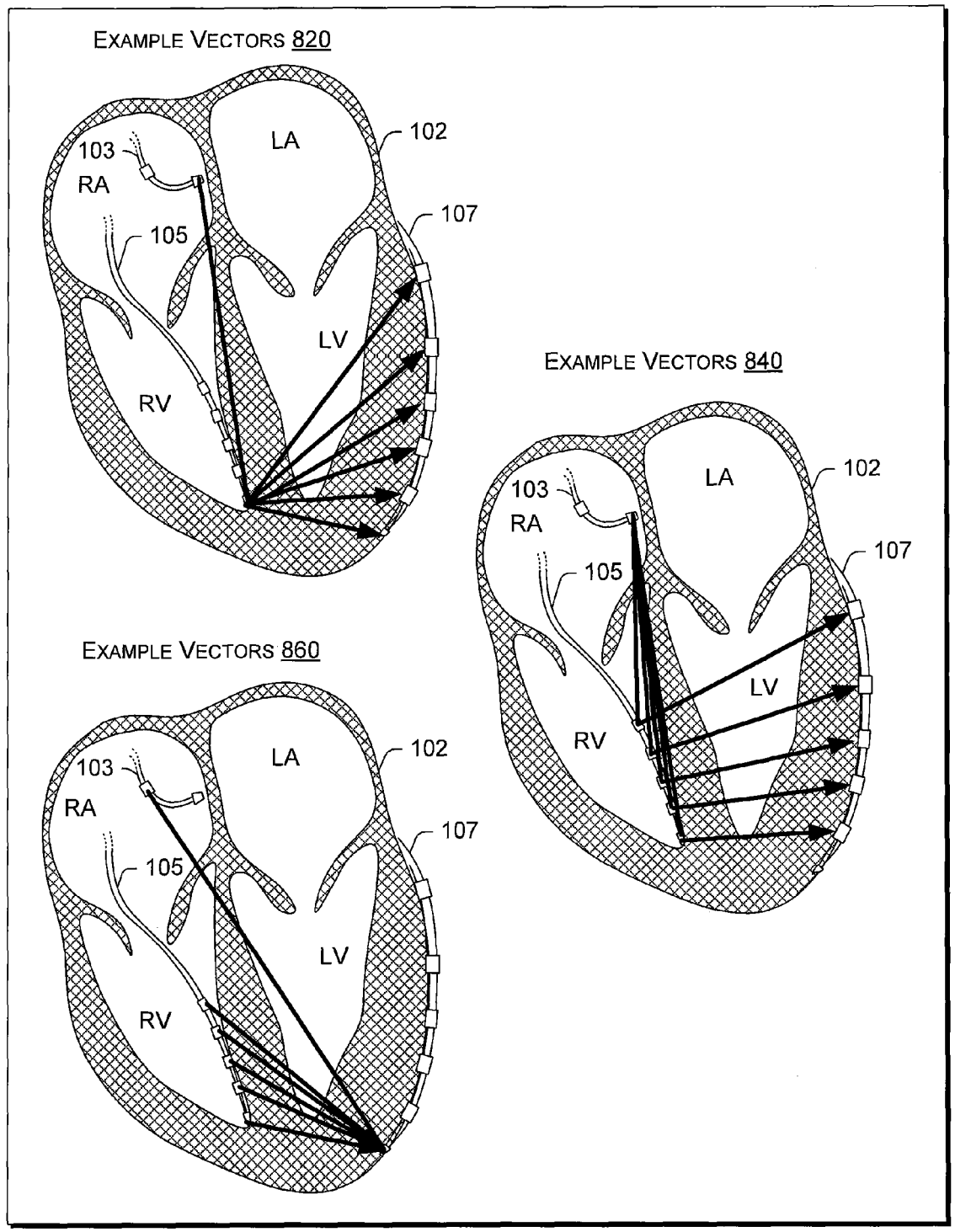
FIG. 8 is a diagram of various examples of RV-to-LV vectors.

FIG. 8 shows cross-sectional views of the heart to illustrate various vectors or sets of vectors; noting that the techniques described herein may rely on vectors or sets of vectors other than those shown in FIG. 8. The example vectors 820 are shown with respect to a right atrial electrode of a right atrial lead 103, a tip or distal electrode of a right ventricular lead 105 and various electrodes of a multi-polar left ventricular lead 107 (e.g., a coronary sinus lead). The example vectors 840 are shown with respect to a right atrial electrode of a right atrial lead 103, electrodes of a multi-polar right ventricular lead 105 and electrodes of a multi-polar left ventricular lead 107. The example vectors 860 are shown with respect to a right atrial electrode of a right atrial lead 103, electrodes of a multi-polar right ventricular lead 105 and a tip or distal electrode of a ventricular lead 107.

Figure 9:
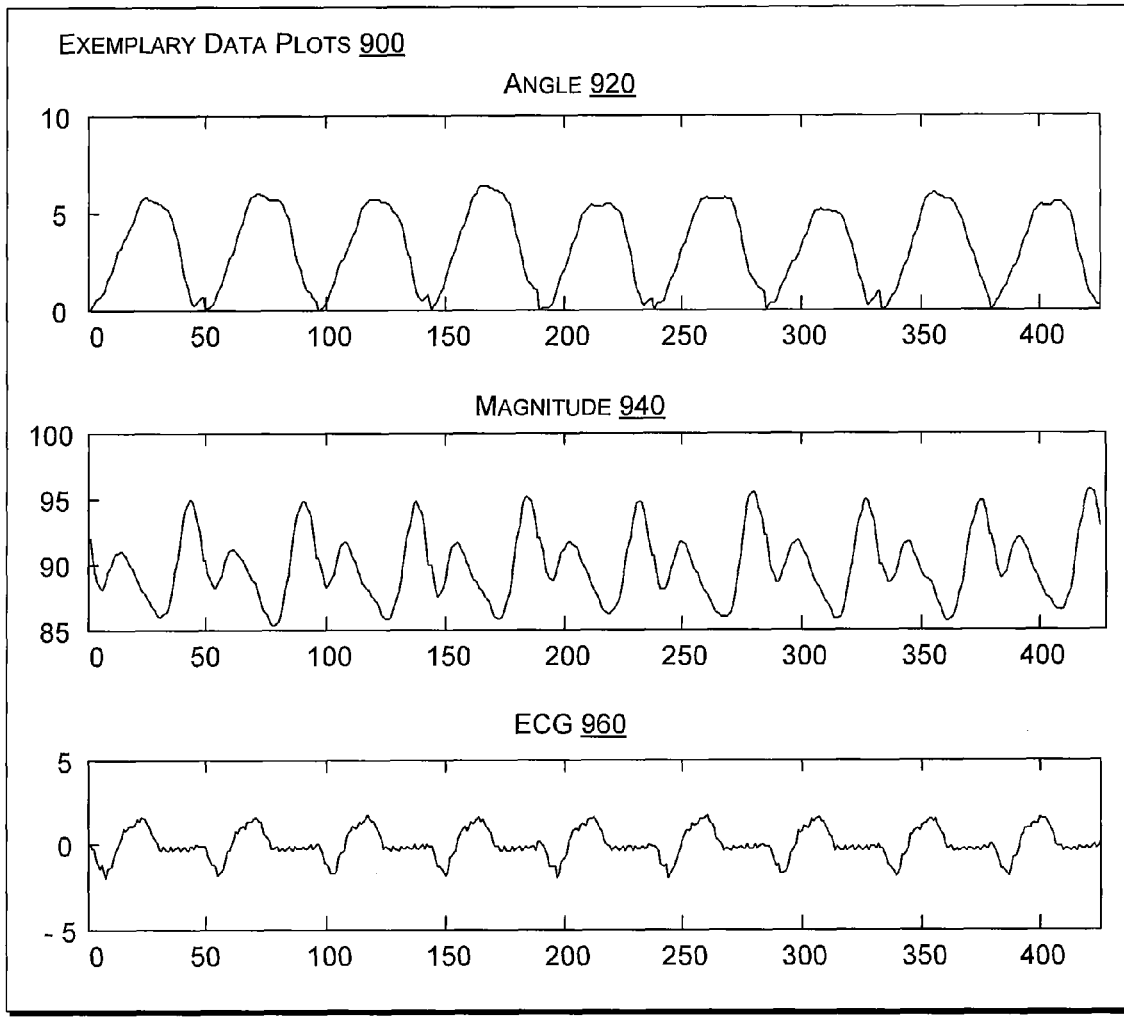
FIG. 9 is a series of plots for vector angle and vector magnitude metrics over a series of paced cardiac cycles and a block diagram of exemplary modules for calculating various vector metrics.
Figure 9:
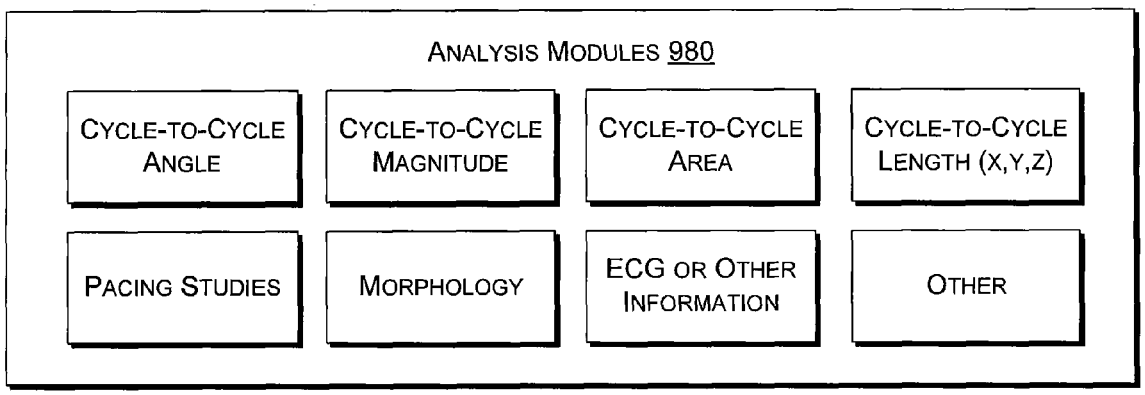

FIG. 9 shows a series of plots 900 for a vector angle metric 920 and a vector magnitude metric 940 over a series of paced cardiac cycles along with a surface ECG 960 and a block 980 of exemplary modules for calculating various vector metrics. The plot 920 shows angle in degrees, which indicates that during a cardiac cycle, the RV-to-LV vector rotates about 6 degrees in clockwise and counter-clockwise directions. The plot 940 shows magnitude in millimeters and indicated that, during a cardiac cycle, the RV-to-LV vector extends and contracts within a range of about 10 mm (e.g., about 1 cm).

The trial data shown in the plots 900 of FIG. 9 demonstrate that the waveforms of magnitude and angle are repeatable for each paced beat. Further, when maximum angle is achieved, magnitude is at its minimum, representing the farthest extent of contraction and rotation of the heart. If this correlation is not achieved due to inherent delay, an exemplary method may use the magnitude waveform and ECG to determine RV-to-LV vector amplitude. Further, if the time of peak angular rotation does not align with the time of peak-minimum distance, this indicates some dissociation of myocardial shortening from twist, indicative of pathologic dyssynchrony.

As described herein, an exemplary method can rely on a vector angle metric, a vector magnitude metric or a combination of angle and magnitude metrics to optimize parameters settings for an implantable device. For example, to assist a clinician in choosing optimal device parameters (e.g., in an acute setting with the ENSITE® NAVX® system).

As described herein, an exemplary method can rely on a vector angle metric, a vector magnitude metric or a combination of angle and magnitude metrics to optimize placement of one or more leads or electrodes associated with an implantable device. For example, to assist a clinician in choosing an optimal lead location (e.g., in an acute setting with the ENSITE® NAVX® system).

As described herein, an exemplary method can rely on a vector angle metric, a vector magnitude metric or a combination of angle and magnitude metrics to optimize a stimulation vector associated with an implantable stimulation device. For example, to assist a clinician in choosing an optimal electrode configuration for a pacing vector (e.g., in an acute setting with the ENSITE® NAVX® system).

In the example of FIG. 9, the analysis modules 980 include a cycle-to-cycle angle module, a cycle-to-cycle magnitude module, a cycle-to-cycle area module, a cycle-to-cycle length module, a pacing studies module, a morphology module, a ECG or other information module and an "other" module (e.g., for other data acquisition, analysis, etc., related to cardiac performance, a therapy, a device, etc.). The modules 980 may be provided as instructions executable by one or more processors of an implantable device or an external device or both an implantable device and an external device (e.g., wholly or in part). Such instructions may be stored in one or more computer-readable media and optionally transmitted using wireless technology (e.g., from an external device to an implanted device).

Figure 10:
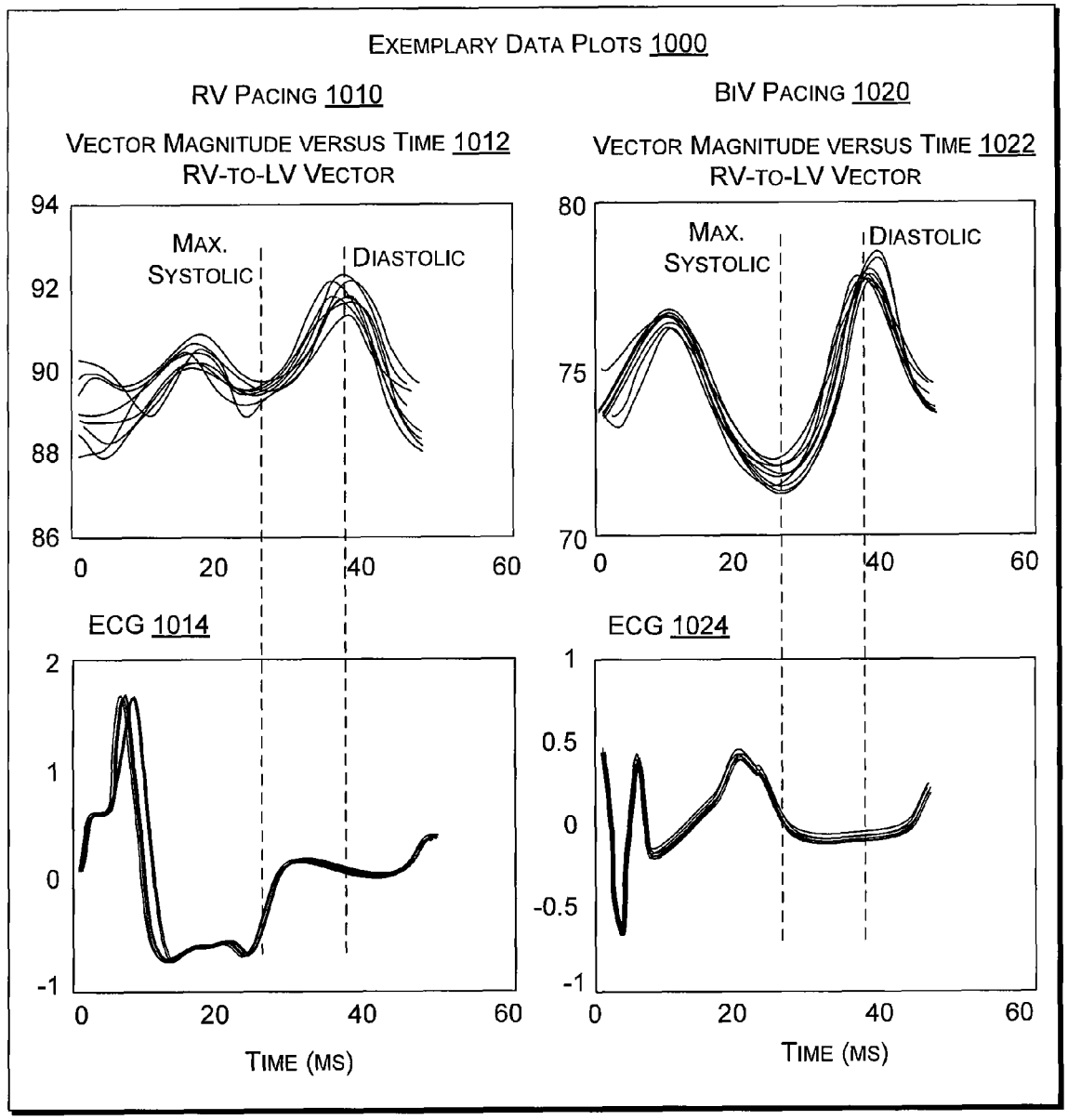
FIG. 10 is a series of plots for RV-to-LV vector magnitude for RV pacing and for biventricular pacing along with associated ECGs.

FIG. 10 is a series of plots 1000 for a vector metric for RV pacing 1010 and for biventricular pacing 1020 along with associated ECGs. Specifically, for RV pacing 1010, a vector magnitude versus time plot 1012 is shown along with a surface ECG 1014 while for BiV pacing 1020, a vector magnitude versus time plot 1022 is shown along with a surface ECG 1024. Vertical dashed lines are shown for the RV pacing 1010 and BiV pacing 1020 data. In the plots 1012 and 1022, the vector magnitude is given in an unscaled distance, which can be scaled to millimeters, for example, given field gradient data.

For RV pacing 1010, the plot 1012 shows that the RV-to-LV vector has a magnitude differential of about 4 mm over a cardiac cycle while for BiV pacing 1020, the plot 1022 shows that the RV-to-LV vector has a magnitude differential of about 7 mm over a cardiac cycle. Based on this data, one may conclude that the BiV pacing scenario 1020 provides for better cardiac performance when compared to the RV pacing scenario 1010. A clinician may rely on such information when setting-up an implantable device. Further, the clinician may adjust location or parameters in a manner to increase the magnitude differential for a selected pacing scenario. The clinician may also examine one or more metrics indicative of consistency. For example, the plot 1012 shows more cycle-to-cycle variation than the plot 1022; hence, the BiV pacing scenario 1020 may be deemed to be more consistent (e.g., beneficial for a patient and/or a device).

Figure 11:
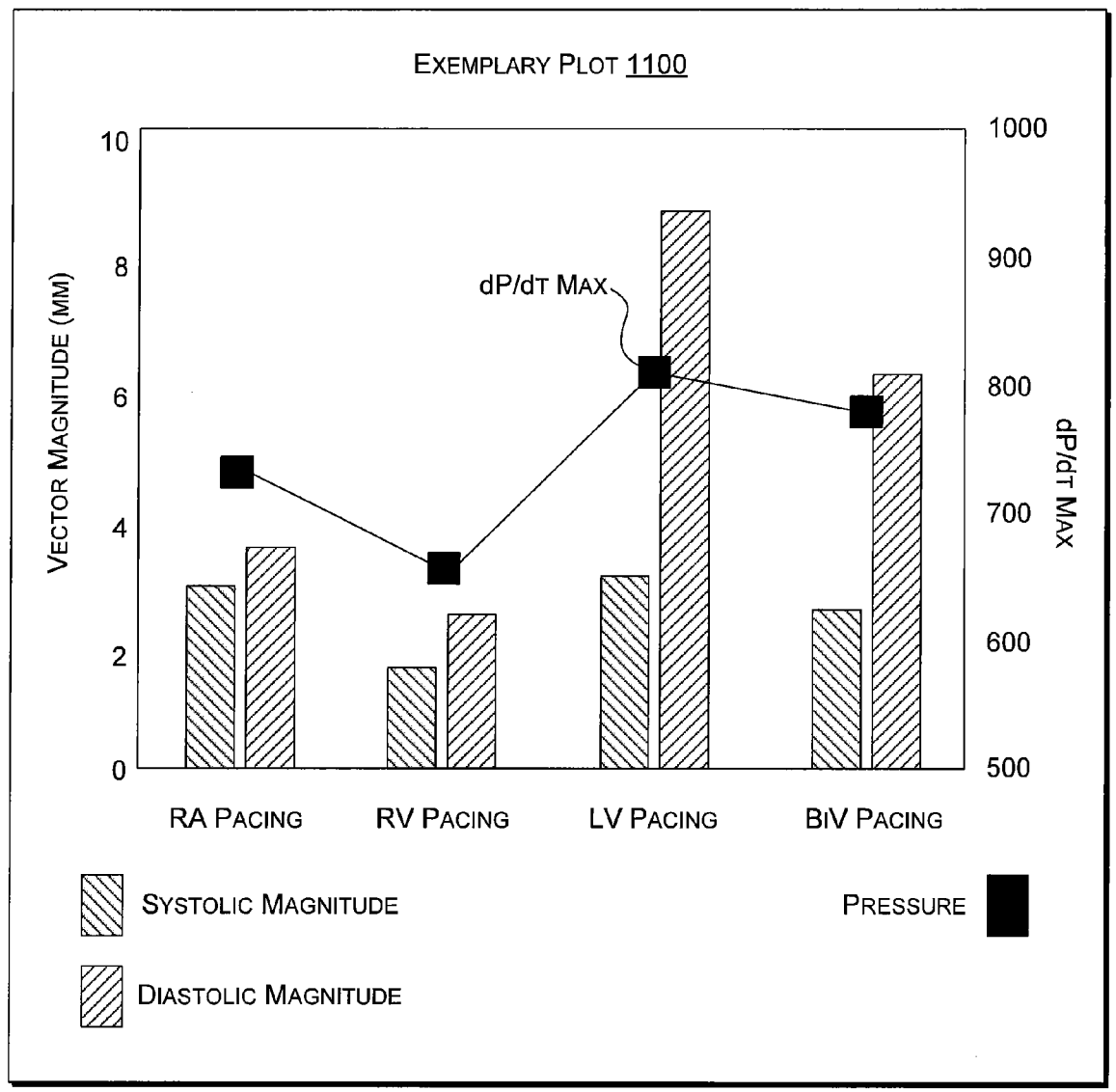
FIG. 11 is a plot of systolic and diastolic RV-to-LV vector magnitude and cardiac chamber pressure for various pacing schemes (RA pacing, RV pacing, LV pacing and BiV pacing), which demonstrates how RV-to-LV vector magnitude, as a metric, can be a surrogate to cardiac chamber pressure.

FIG. 11 shows a plot 1100 of systolic and diastolic RV-to-LV vector magnitude and cardiac chamber pressure for various pacing schemes (RA pacing, RV pacing, LV pacing and BiV pacing), which demonstrates how RV-to-LV vector magnitude, as a metric, can be a surrogate to cardiac chamber pressure. For all schemes, the systolic magnitude is less than the diastolic magnitude. Further, a differential may be defined as the diastolic magnitude minus the systolic magnitude. An exemplary method may rely on such a differential metric to optimize one or more aspects of a therapy (e.g., electrode location, pacing mode, one or more delays, etc.).

In the plot 1100, filled squares correspond to maximum pressure (change in pressure with respect to time). Pressure is an accepted hemodynamic measure for assessing cardiac performance and, in particular, the maximum change in pressure with respect to time ($dP/dt_{max}$). Pressure change with respect to time is shown in FIG. 11 to demonstrate that the exemplary RV-to-LV vector magnitude metric correlates with an accepted standard invasive pressure measure. For the plot 1100, LV pressure data were acquired using a Millar pressure sensor (e.g., Ultra-Miniature MIKRO-TIP®, Millar Instruments, Inc., Texas).

As demonstrated by the data of the plot 1100, the RV pacing condition produced the smallest vector magnitudes and the lowest maximum LV pressure change for a cardiac cycle (i.e., worst condition); whereas, the LV pacing condition produced the largest vector magnitudes and vector magnitude differential and the highest maximum LV pressure change for a cardiac cycle (i.e., best condition). The results also indicate that the tested biventricular pacing condition performs quite similarly to the tested LV pacing condition.

Figure 12:
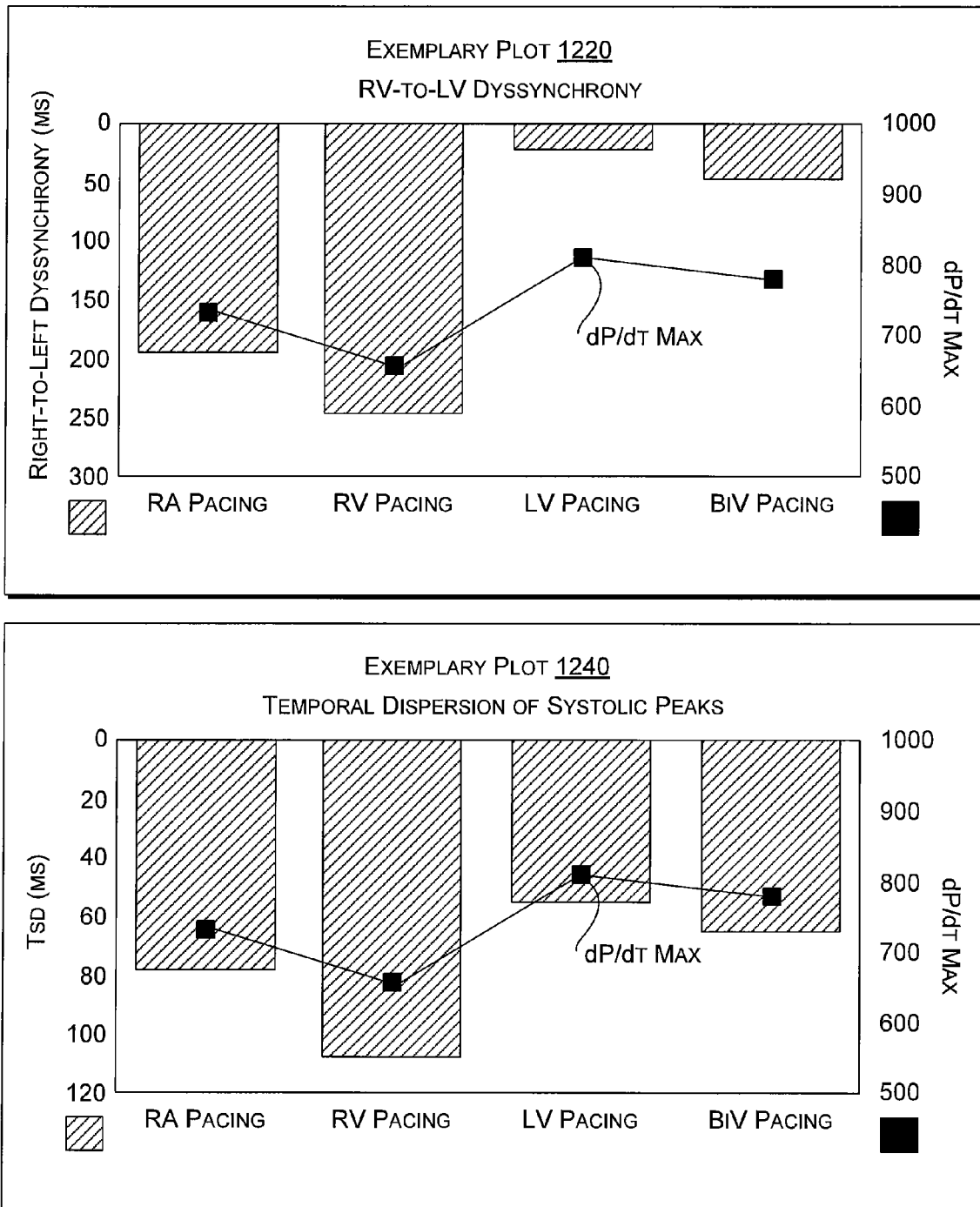
FIG. 12 is a series of plots for ventricular dyssynchrony and temporal dispersion of systolic peaks of individual electrodes for various pacing schemes (RA pacing, RV pacing, LV pacing and BiV pacing).

FIG. 12 shows a plot 1220 and a plot 1240 of trial data for right atrial pacing (RA pacing), right ventricular pacing (RV pacing), left ventricular pacing (LV pacing) and biventricular pacing (BiV pacing). The plot 1220 provides bars that correspond to right-to-left dyssynchrony in milliseconds (ms) on an inverted scale and filled squares that correspond to maximum dP/dt (change in pressure with respect to time). The plot 1240 provides bars that correspond to temporal dispersion of systolic peaks in milliseconds (ms) on an inverted scale and filled squares that correspond to maximum pressure (change in pressure with respect to time). As mentioned, pressure is an accepted hemodynamic measure for assessing cardiac performance and, in particular, the maximum change in pressure with respect to time (dP/dt). Pressure change with respect to time is shown in FIG. 12 to demonstrate that the exemplary right-to-left dyssynchrony metric and the temporal dispersion metric correlate with an accepted standard invasive pressure measure.

As demonstrated by the data of the plots 1220 and 1240, the RV pacing condition produced the greatest right-to-left dyssynchrony, the greatest temporal dispersion of systolic peaks and the lowest maximum LV pressure change for a cardiac cycle (i.e., worst condition); whereas, the LV pacing condition produced the smallest right-to-left dyssynchrony, the smallest temporal dispersion of systolic peaks and the highest maximum LV pressure change for a cardiac cycle (i.e., best condition). The results also indicate that the tested biventricular pacing condition performs quite similarly to the tested LV pacing condition. Various exemplary approaches described herein may include a vector analysis where one or more vector metrics are used to assess cardiac performance, for example, with respect to a pacing configuration (e.g., a vector analysis can provide a right-to-left dyssynchrony metric and a vector analysis can provide a temporal dispersion metric).

Figure 13:
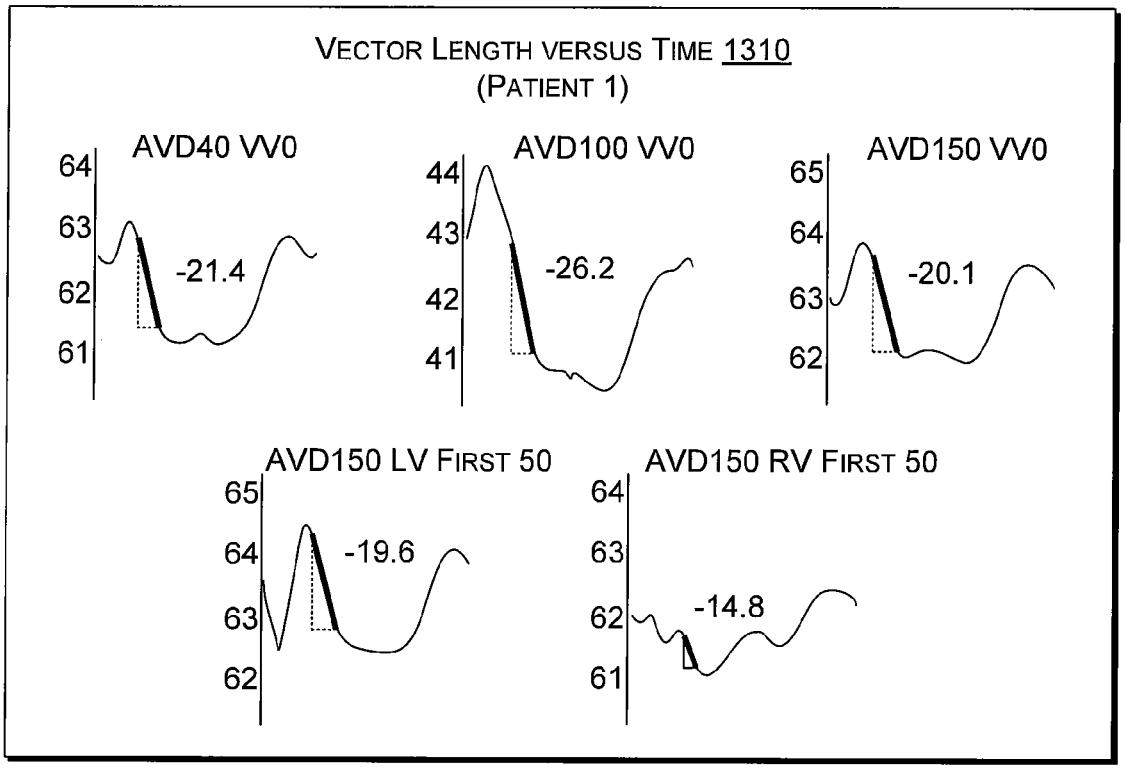
FIG. 13 is a series of plots of RV-to-LV vector length versus time for two patients for various pacing schemes (i.e., various delays, RV first and LV first).
Figure 13:
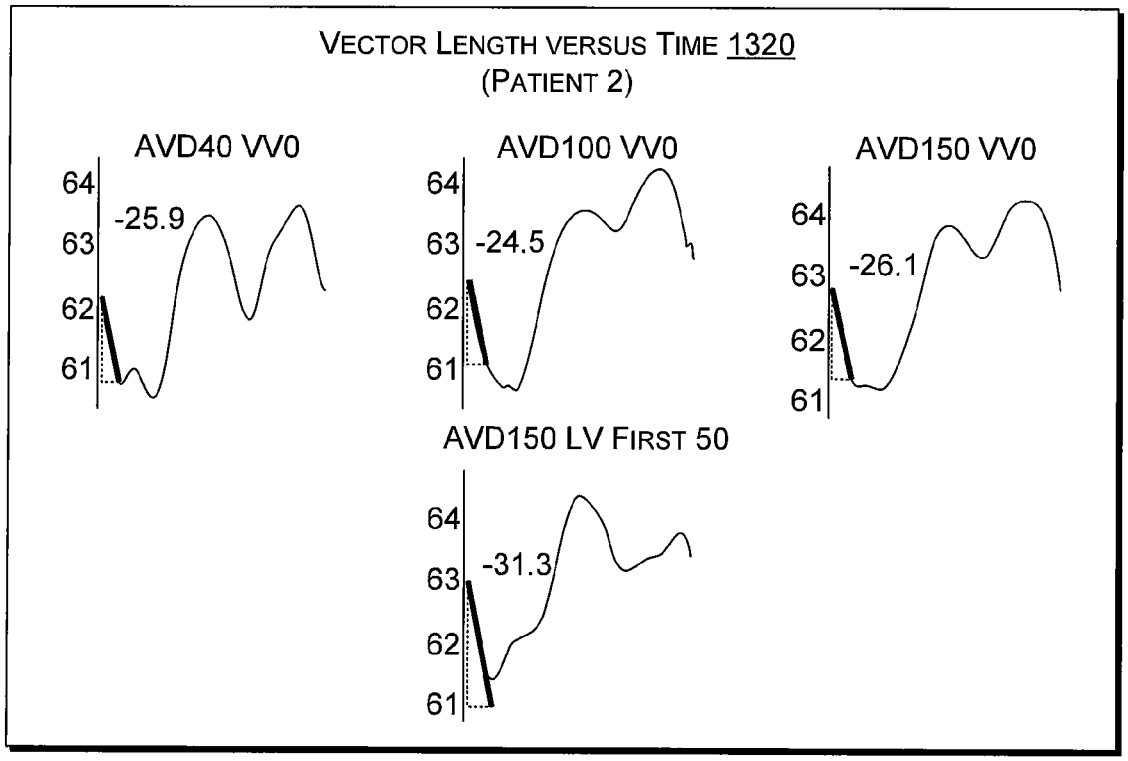

FIG. 13 shows a series of plots of RV-to-LV vector length versus time for two patients for various pacing schemes (i.e., various delays, RV first and LV first). Plots 1310 for a first patient include biventricular pacing scenarios with a VV of 0 ms (RV and LV paced simultaneously) and atrio-ventricular delays (AVD) of 40 ms, 100 ms and 150 ms and biventricular scenarios where, with an AVD of 150 ms, the LV is paced 50 ms prior to the RV and where the RV is paced 50 ms prior to the LV. The plots 1310 show slopes (e.g., systolic slopes) as associated with a change in RV-to-LV vector length with respect to time. The greatest negative slope (−26.2 mm/ms) occurs for an AVD of 100 ms and VV of 0 ms where the vector has a differential of about 3 mm to 4 mm over a cardiac cycle. In contrast, the scenario for an AVD of 150 ms and RV first by 50 ms (VV=50 ms or −50 ms, depending on convention) has a slope of −14.8 mm/ms and a differential of about 1 mm to 2 mm over a cardiac cycle. Such an analysis may assist a clinician in setting one or more parameters of a pacing configuration for delivery of a therapy (e.g., CRT).

Plots 1320 for a second patient include biventricular pacing scenarios with a VV of 0 ms and atrio-ventricular delays (AVD) of 40 ms, 100 ms and 150 ms and a biventricular scenario where, with an AVD of 150 ms, the LV is paced 50 ms prior to the RV. The plots 1320 show slopes (e.g., systolic slopes) as associated with a change in RV-to-LV vector length with respect to time. The greatest negative slope (−31.3 mm/ms) occurs for an AVD of 150 ms and a VV of 50 ms (LV first) where the vector has a differential of about 3 mm to 4 mm over a cardiac cycle. Such an analysis may assist a clinician in setting one or more parameters of a pacing configuration for delivery of a therapy (e.g., CRT).

Figure 14:
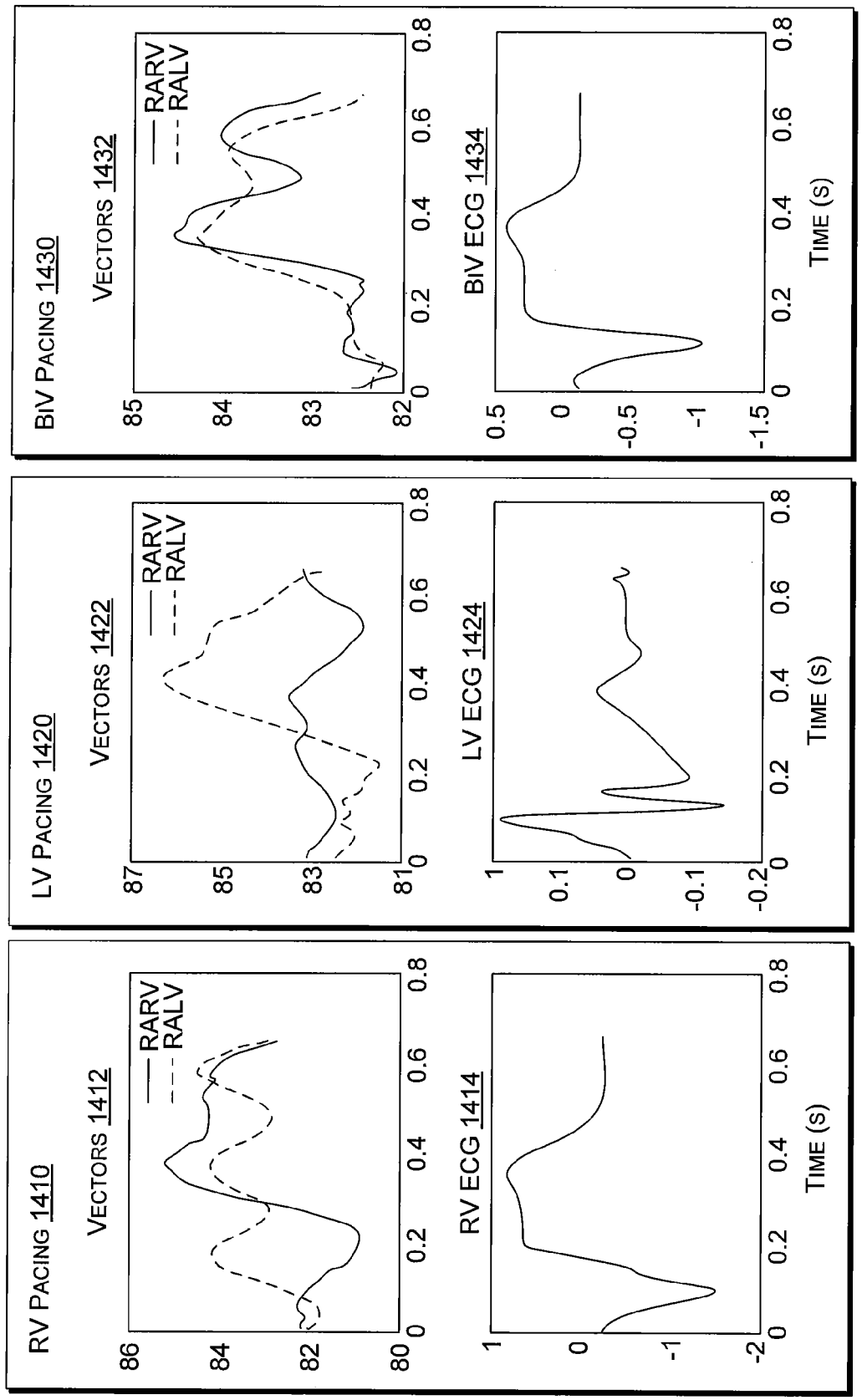
FIG. 14 is a series of plots for RA-to-RV vector magnitude and RA-to-LV vector magnitude versus time for RV pacing, LV pacing and biventricular pacing schemes along with associated ECGs.

FIG. 14 is a series of plots for RV pacing 1410, LV pacing 1420 and biventricular pacing 1430 schemes. The plots include RA-to-RV vector magnitude and RA-to-LV vector magnitude versus time plots 1412, 1422 and 1432 along with associated ECGs 1414, 1424 and 1434, for RV pacing 1410, LV pacing 1420 and biventricular pacing 1430, respectively.

The vector metric plots 1412, 1422 and 1432 demonstrate how the heart moves responsive to RV pacing 1410, LV pacing 1420 and biventricular pacing 1430 scenarios, respectively. The plot 1412 shows that, for the RV pacing scenario 1410, the displacement of the RA-to-RV vector is greater than that of the RA-to-LV vector. The plot 1422 shows that, for the LV pacing scenario 1420, the displacement of the RA-to-RV vector is less than that of the RA-to-LV vector. The plot 1432 shows that, for the BiV pacing scenario 1430, the displacement of the RA-to-RV vector is about the same as that of the RA-to-LV vector.

Figure 15:
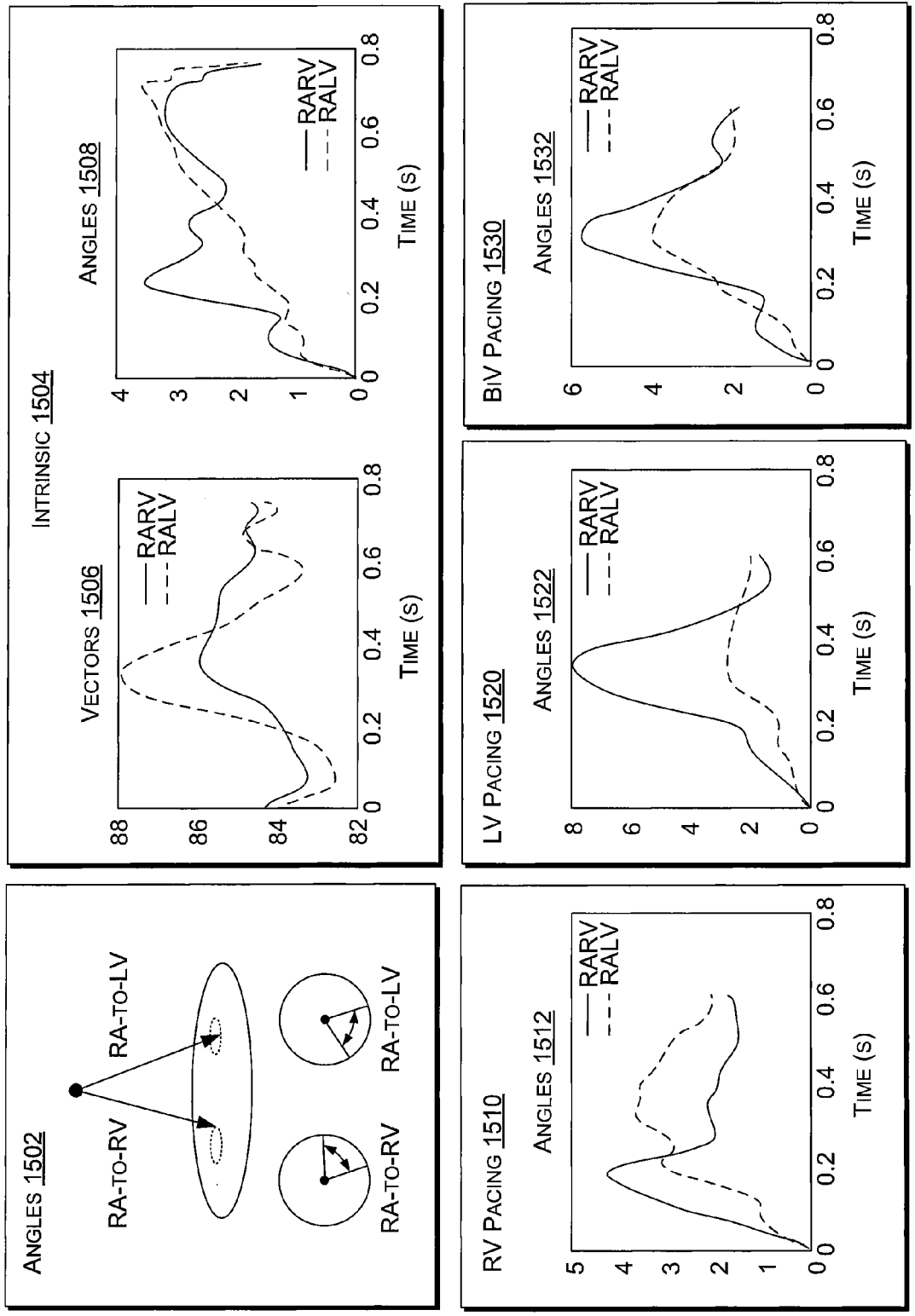
FIG. 15 is a diagram of various vectors and a series of plots of vector magnitude and vector angle with respect to time.

FIG. 15 is a diagram of vector angles 1502 and a series of plots for intrinsic activation 1504, RV pacing 1510, LV pacing 1520 and biventricular pacing 1530 schemes. The vector angles diagram 1502 indicates angular movement of a RA-to-RV vector and a RA-to-LV vector during a cardiac cycle. For intrinsic activation 1504, a vector magnitude plot 1506 for a RA-to-RV vector and a RA-to-LV vector demonstrates increased displacement for the RA-to-LV vector compared to the RA-to-RV vector during a cardiac cycle. A vector angle plot 1508 shows how angle changes for each vector during the cardiac cycle. In this trial, the angle for the RA-to-LV vector shows a relatively constant slope to a maximum value while the RA-to-RV vector shows two approximately equal maxima.

The angle plots 1512, 1522 and 1532 correspond to the vector plots 1412, 1422 and 1432 of FIG. 14. An analysis of the angle plots 1512, 1522, 1532 demonstrates how the biventricular pacing scenario 1530 improves synchrony (e.g., reduces dyssynchrony) compared to the intrinsic scenario 1504. Specifically, the biventricular pacing scenario 1530 acts to synchronize time to angular peak for both the RA-to-RV vector and the RA-to-LV vector.

Figure 16:
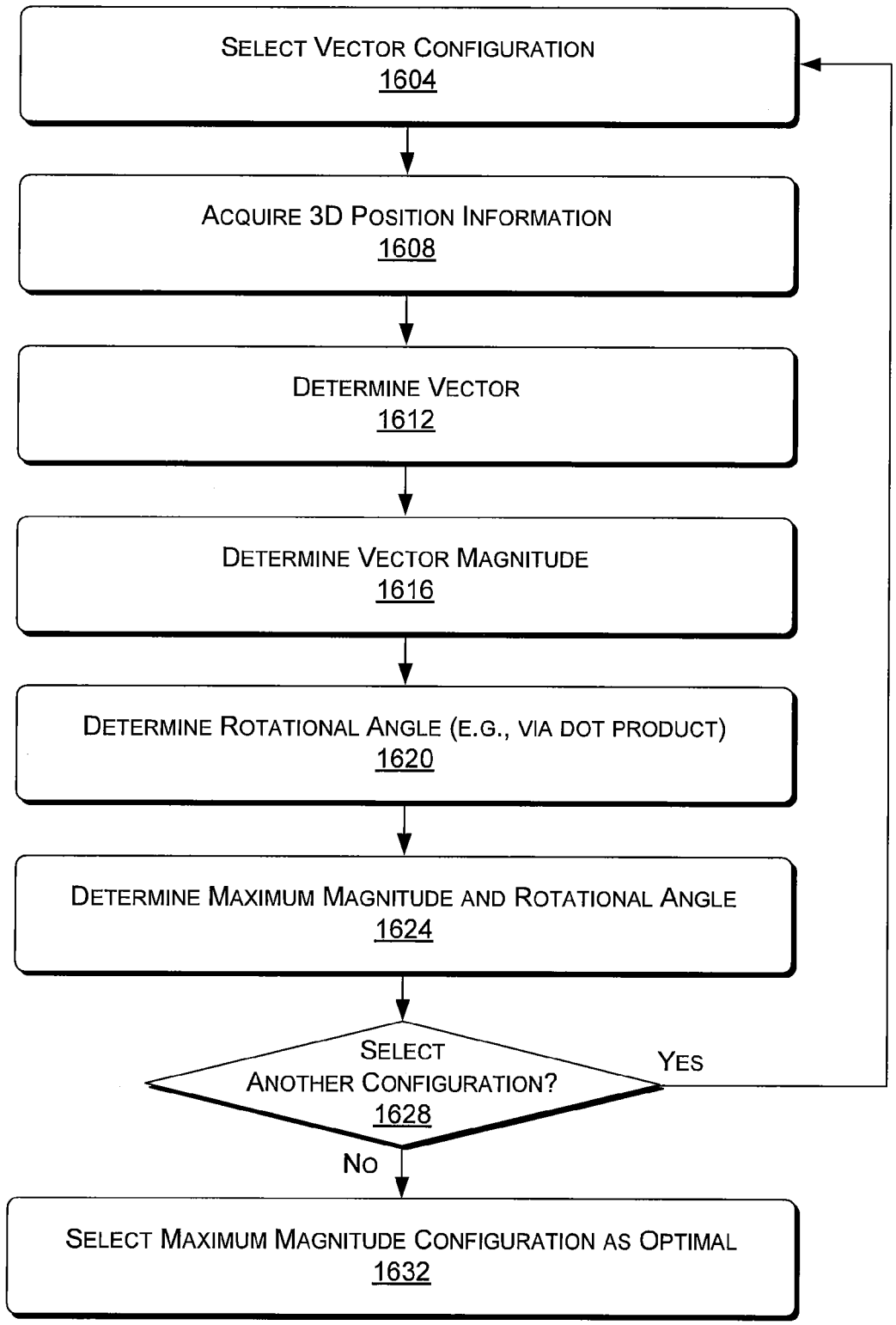
FIG. 16 is a block diagram of an exemplary method for selecting an optimal configuration based at least in part on vector metrics.

FIG. 16 shows a block diagram of an exemplary method 1600 for selecting an optimal configuration based at least in part on vector metrics. In a selection block 1604, a vector configuration is selected (see, e.g., the block 310 of FIG. 3 and the block 410 of FIG. 4). In an acquisition block 1608, three-dimensional position information is acquired for the selected vector configuration. In a determination block 1612, the vector coordinates or position(s) are determined based on the acquired position information.

Once the vector is defined and position information provided, one or more determination blocks can calculate one or more vector metrics. For example, in the method 1600, a vector magnitude determination block 1616 determines vector magnitude while a vector rotational angle determination block determines vector rotational angle (e.g., with respect to a reference vector as described with respect to FIG. 6 or see, e.g., vector diagram 1502 of FIG. 15).

Given one or more vector metrics, an analysis block 1624 may determine a maximum or maxima, a minimum or minima, a differential or differentials, a derivative or derivatives, an area or areas, etc., of the vector metrics (e.g., optionally with respect to time, events, phase of a cardiac cycle, etc.). The analysis block 1624 may call for storing information to memory, for example, to perform additional analyses or to recall results of an analysis.

In the example of FIG. 16, the method 1600 continues to a decision block 1628 that decides whether another configuration is to be selected. If so, the method 1600 returns to the selection block 1604. If another configuration is not to be selected, the method 1600 enters a selection block 1632 that selects an optimal configuration, which may be one of the configurations tested or a suggested, optimal configuration based on an analysis of one or more tested configurations. In the example of FIG. 16, the selection block 1632 acts to select a configuration, amongst multiple tested configuration, with the maximum vector magnitude (e.g., where the method 1600 has tested more than one configuration).

Figure 17:
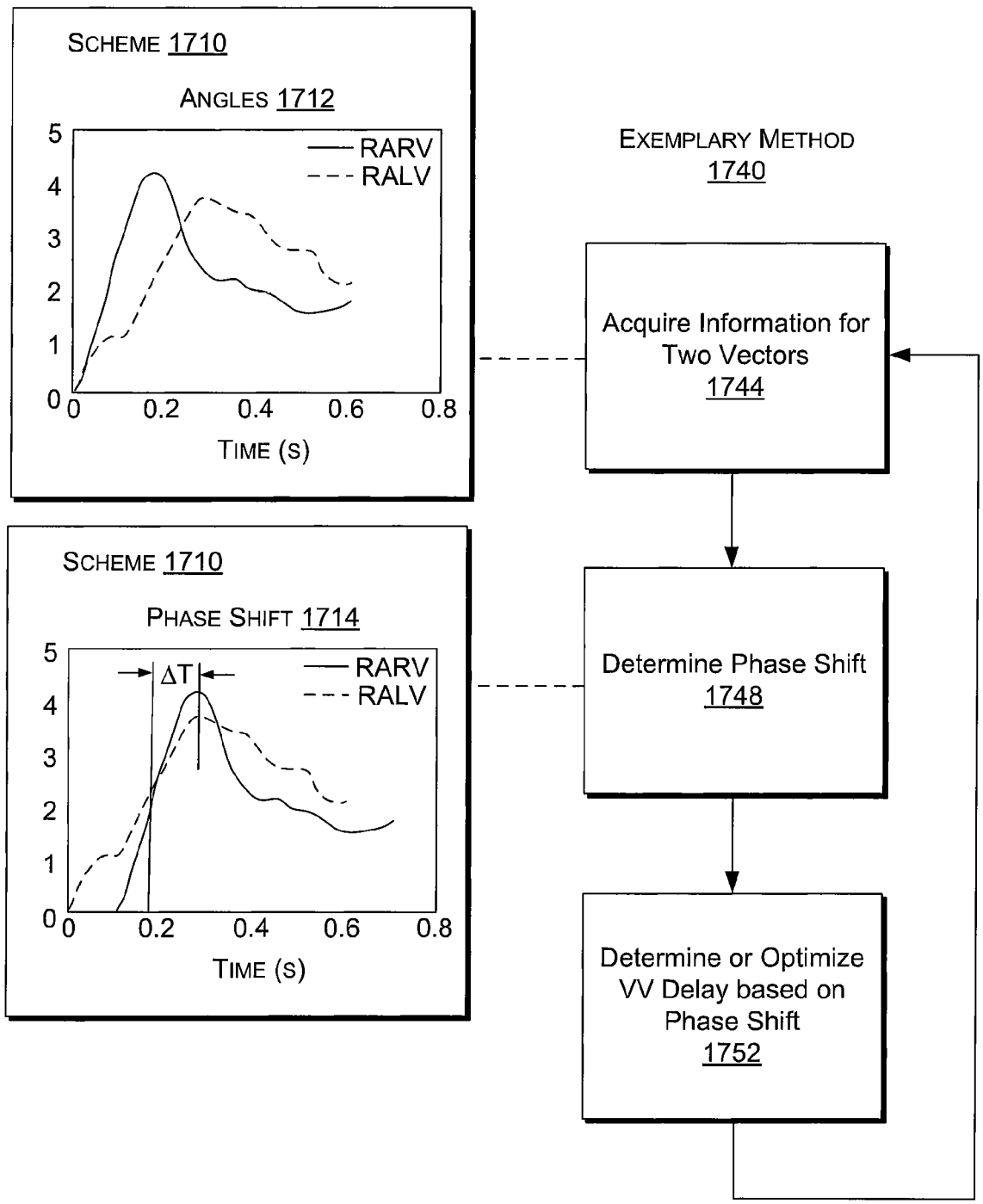
FIG. 17 is a block diagram of an exemplary method for determining or optimizing a VV delay based on an analysis of vectors.

FIG. 17 shows an exemplary method 1740 with reference to a pacing scheme 1710. In an acquisition block 1744, information is acquired for two vectors during at least a portion of a cardiac cycle. For example, a plot 1712 shows angles for two vectors over at least a portion of a cardiac cycle. A determination block 1748, determines a phase shift for the two vectors. For example, such a phase shift may be determined according to a phase shift plot 1714 where the phase shift is equal to a time difference ($\Delta T$) between peak angles for the two vectors. Accordingly, the time difference ($\Delta T$) may be relied on as an indicator of dyssynchrony (i.e., a dyssynchrony metric). A determination or optimization block 1752 follows that can determine a VV delay value based on the phase shift or optimize an existing VV delay. For example, in an iterative manner, an initial iteration may determine an initial shift for use as a VV delay. In a subsequent iteration, the method 1740 may be repeated, commencing at the acquisition block 1744. In such a manner, the VV delay is updated until the shift reaches some acceptable minimum according to a predefined parameter (e.g., a few milliseconds). Hence, as described herein, an analysis of data for two vectors may be used to determine or optimize VV delay.

Various exemplary methods described herein include vector analysis to optimize cardiac therapy such as CRT. Various methods rely on RA-to-RV and RA-to-LV vectors and associated features as indicators of mechanical dyssynchrony. In general, the vectors are defined by electrodes where the electrodes may be tracked with respect to time over at least a portion of a cardiac cycle. Various examples include acquisition of motion information for RA, RV and LV electrodes (e.g., associated with a CRT system).

As described herein, vector information may be acquired with respect to time and presented as vector waveforms. For example, the plots 1412, 1422 and 1432 of FIG. 14 and the plots 1506, 1508, 1510, 1520 and 1530 of FIG. 15 show vector waveforms (e.g., vector magnitude waveforms and vector angle waveforms).

Various exemplary methods include statistical analysis. For example, a method can include a correlation analysis to generate a correlation coefficient that indicates strength and direction of a linear relationship between two variables (e.g., vectors). Where a correlation coefficient approaches 1, a strong linear relationship exists; whereas, as a correlation coefficient approaches −1, a decreasing linear relationship exists. The closer a correlation coefficient is to either −1 or 1, the stronger the correlation between the variables. In a geometric interpretation, for centered data (e.g., data shifted by a sample mean to have an average of zero), a correlation coefficient can be represented as the cosine of the angle between two vectors of samples drawn from the two variables.

In statistics, the term cross-covariance is sometimes used to refer to the covariance cov(X, Y) between two random vectors X and Y, in order to distinguish that concept from the "covariance" of a random vector X, which is understood to be the matrix of covariances between the scalar components of X. In signal processing, the cross-covariance is a measure of similarity of two signals. Cross-covariance is a function of the relative time between two signals and is sometimes called the sliding dot product (e.g., with applications in pattern recognition).

As described herein, an exemplary method includes statistical analysis of a RA-to-RV vector waveform and a RA-to-LV vector waveform. Such an analysis may be used as an indicator of dyssynchrony, for example, for acute CRT optimization or chronic CRT optimization. Such an index may be calculated by a cross-covariance technique, in which a value of 1 represents 100% synchrony and a value of −1 represents 100% dyssynchrony (e.g., "anti-synchrony" or negative synchrony). A value of about 0 may represent somewhat independent behavior of the two vectors. In general, as a value becomes closer to 1, the therapy provides for better synchrony (e.g., a desired result of CRT).

In an exemplary method, a lead can be placed by intrapericardial procedure at an epicardial surface or placed endocardially inside a cardiac chamber (e.g., including LA and LV). In such an example, positions from other available electrodes (e.g., from other diagnostic or therapeutic devices, including EP catheters, guidewires, stylets or delivery tools) can be tracked as well.

An exemplary system that includes a RA-to-RV vector and a RA-to-LV vector can be defined by tip electrode positions for RA, RV and LV leads where the RA tip coordinate is (X1, Y1, Z1), the RV tip coordinate is (X2, Y2, Z2) and the LV tip coordinate is (X3, Y3, Z3). Given this notation, a formula for the calculation can be given as:

$$|\overrightarrow{RARV}| = \sqrt{(x_2-x_1)^2+(y_2-y_1)^2+(z_2-z_1)^2}$$

$$|\overrightarrow{RALV}| = \sqrt{(x_3-x_1)^2+(y_3-y_1)^2+(z_3-z_1)^2}$$

As described herein, a cross-covariance coefficient may be used as a dyssynchrony index. For discrete functions $f_i$ and $g_i$ the cross-covariance is defined as:

$$cov(j) \Sigma i=1:n f^*(j) g(j+i)$$

where the sum is over the appropriate values of the integer j and an asterisk indicates the complex conjugate. For continuous functions f(x) and $g_i$ the cross-covariance is defined as:

$$(f*g)(x) \stackrel{def}{=} \int f*(t)g(x+t)dt$$

where the integral is over the appropriate values of t.

As described herein, an exemplary method may apply a simple regression technique for data associated a RA-to-RV vector and a RA-to-LV vector. For example, given such an approach, if the mean squared error (MSE) is at a minimum, then a result may be considered optimal.

As described herein, an exemplary dyssynchrony index can be calculated by a cross-covariance technique to define similarity between RA-to-RV vector and RA-to-LV vector distance waveforms. This index represents the synchrony for both time and amplitude features simultaneously. In an alternative approach, individual features of two waveforms, such as time to a peak, valley, or inflection, or the value at a peak, valley, or inflection can be used instead of an entire waveform morphology. Accordingly, a correlation between time and/or value of one or more features can be used as a dyssynchrony index. For example, where the RV and LV contract at the same time, the RA-to-RV vector and RA-to-LV vector waveforms should coincide not only for time features, but also for amplitude features. On the other hand, if the RA-to-RV vector and the RA-to-LV vector are misaligned, then both time and amplitude features for these two vectors will be opposed to each other. Subtraction techniques may be optionally used to subtract one waveform from another waveform where the resulting waveform may be analyzed (e.g., mathematically, for morphology, etc.) to aid in diagnosis, selecting a configuration, etc.

As described herein, an exemplary method includes computing features of a RA-to-RV vector and a RA-to-LV vector waveform. For example, area under each waveform may be compared and a dyssynchrony index defined as a difference (optimal==0) or quotient (optimal==1) between the areas. Further, area between two waveforms can be computed where an index (e.g., optimal==0) is defined as the area between the two waveforms for a portion of a cardiac cycle, a cardiac cycle or several cardiac cycles.

An exemplary method may include calculating a sum, an average, a mean, a product, or a convolution of two vector waveforms (e.g., a RA-to-RV vector waveform and a RA-to-LV vector waveforms). According to such a method, an index may be defined as a peak-to-peak value or a maximum or an average slope value where, the higher the value of the index, the more synchronized the vectors and hence the corresponding chambers or regions of the heart.

While various examples mention vector magnitude or distance, other features may be used, including vector angle. An exemplary approach may also include resolving a 3D vector into one or more components, optionally aligned with a physiologically relevant direction (e.g., a long or short axis of the heart).

Figure 18:
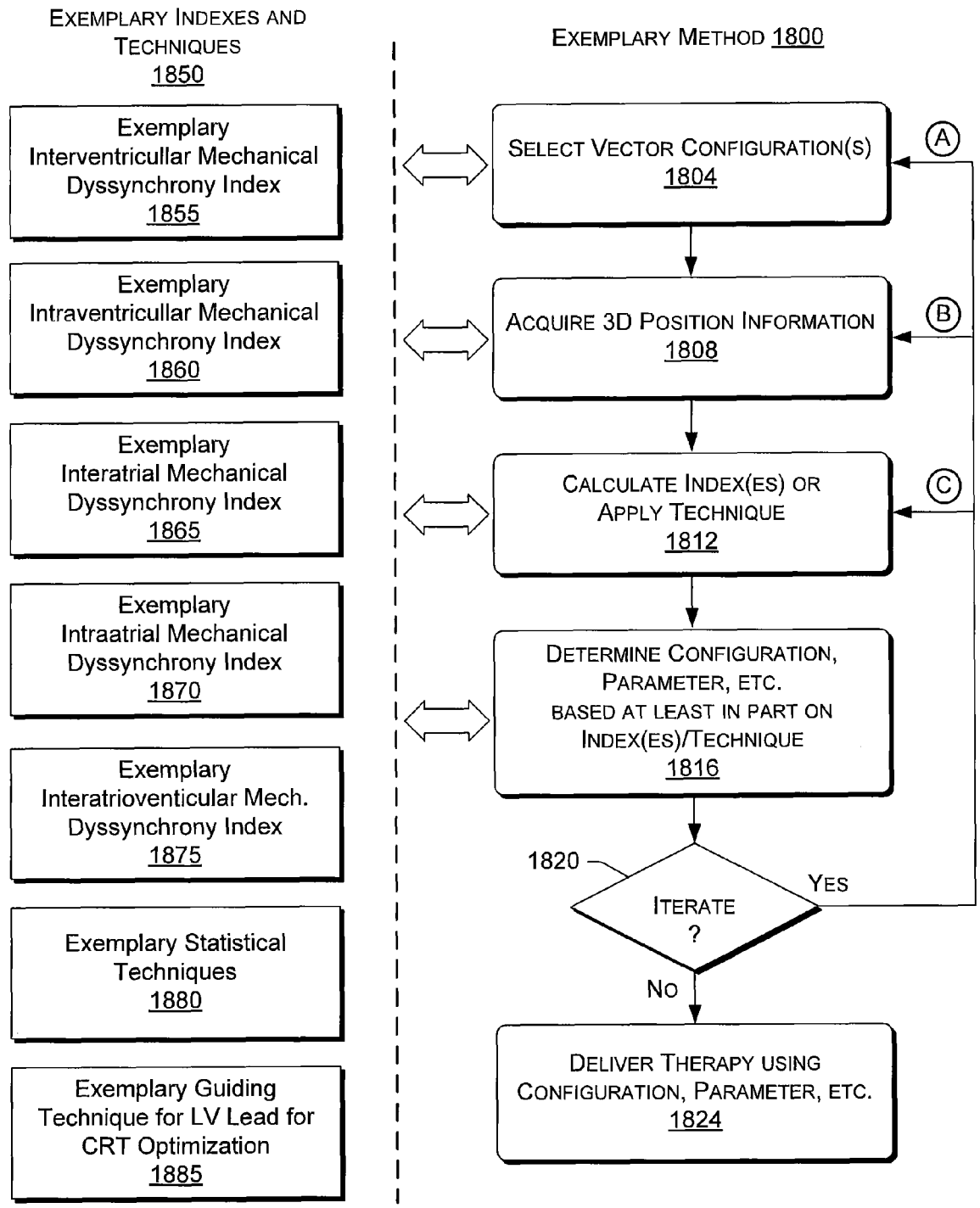
FIG. 18 is a block diagram of an exemplary method and various exemplary indexes and techniques that may be implemented by the method.

FIG. 18 shows an exemplary method 1800 that may rely on one or more exemplary indexes or techniques 1850. As described herein, various metrics are referred to as indexes. For example, a dyssynchrony index can be calculated based on magnitude or angle waveforms for a right ventricular vector and a left ventricular vector. Such a dyssynchrony index may be an interventricular dyssynchrony index 1855. Other types of vector-based indexes include, for example, an intraventricular dyssynchrony index 1860, an interatrial dyssynchrony index 1865, an intraatrial dyssynchrony index 1870 and an interatrioventricular dyssynchrony index 1875. As described herein, various exemplary vector analysis techniques include statistical techniques 1880 such as correlation or cross-covariance. Accordingly, therapy configuration, parameters or configuration and parameters may be determined and optimized using one or more exemplary vector-based methods. For example, an exemplary guiding technique 1885 may optimize position of an LV lead for CRT.

The exemplary method 1800 includes a selection block 1804 that selects one or more vector configurations (e.g., according to one or more of the indexes or techniques 1850). An acquisition block 1808 acquires three-dimensional position information, typically with respect to time (e.g., according to one or more of the indexes or techniques 1850). A calculation block 1812 calculates one or more indexes, applies a technique or a combination thereof (e.g., according to one or more of the indexes or techniques 1850). A determination block 1816 determines one or more of a configuration and a parameter based, at least in part on, the result(s) of the calculation block 1812. A decision block 1820 decides whether to iterate the method 1800, for example, to understand better a scenario, to optimize a configuration, to optimize a parameter, etc. If the decision block 1820 decides to iterate, the method 1800 may continue according to, for example, Option A (selection block 1804), Option B (acquisition block 1808) or Option C (calculation block 1812). If the decision block 1820 decides not to iterate (e.g., optionally after one or more iterations), the method 1800 continues in a delivery block 1824, which configures a therapy using a configuration, parameter, etc., determined at least in part on a vector analysis. For example, the delivery block 1824 may include programming an implantable device to use a certain electrode configuration, a certain delay, etc. The method 1800 may be performed by a computing system in an automated or semi-automated manner, for example, based on control logic. Control logic is, in general, circuitry such as hardware or a combination of hardware and software, which may allow for input by a clinician or other operator. Control logic may be implemented based on instructions stored in a computer-readable memory. For example, an exemplary computer-readable memory can include instructions that configure a computing device to perform various actions of an exemplary method (e.g., selection of vectors, acquisition of information, calculations, determinations, decisions to iterate, etc.).

As explained with respect to FIG. 18, an exemplary method can include calculating an interventricular mechanical dyssynchrony index based on vector features 1855 (e.g., RA-to-RV and RA-to-LV vectors); an exemplary method can include calculating an intraventricular mechanical dyssynchrony index based on vector features 1860 (e.g., RA-to-LV1 and RA-to-LV2 vectors or by placing a multielectrode catheter, or lead, either inside a chamber or inside one or more branches of the coronary sinus (e.g., to aid optimization of electronic repositioning)); an exemplary method can include calculating an interatrial dyssynchrony index based on vector features 1865, for example, by selecting RA-to-RV and LA-to-RV vectors, or other vector configurations (e.g., RA-to-LV and LA-to-LV); an exemplary method can include calculating an intraatrial dyssynchrony index based on vector features 1870 (e.g., various LA or various RA configurations); and an exemplary method can include calculating a vector-based intraatrioventricular dyssynchrony index 1875 by selecting RA-to-LV and RV-to-LV vectors, or other vector configurations (e.g., LA-to-RV, RV-to-LV etc.).

As shown in FIG. 18, an exemplary method for optimization of a CRT device can use one or more vector-based dyssynchrony indexes. For example, in such a method, after one or more leads are placed at a desired position or positions, connections may be made to a localization system (e.g., the ENSITE® NAVX® system) to record 3-D motion for various electrodes. The localization system may then calculate a dyssynchrony index and provide an output, for example, by rendering the information to a display (e.g., optionally with waveform graphs). A clinician may select one or more different types of pacing interventions and acquire further information. A comparison can be made of dyssynchrony indexes for the different scenarios (e.g., pacing intervention, position, etc.) to guide the clinician to an optimum configuration for delivery of a therapy. As indicated FIG. 18, an exemplary system can implement a method 1885 for guiding the LV lead placement by measuring a vector-based dyssynchrony index during an implant procedure or relocation procedure. An exemplary method can include mapping of a coronary sinus by superimposing one or more dyssynchrony indexes over one or more anatomical markers of the coronary sinus. In such an approach, a clinician can determine where to place an LV electrode (e.g., a LV lead) to achieve an optimal pacing effect (e.g., based on reduced mechanical latency).

As explained, various exemplary methods can include statistical analysis of vector-based features. For example, as indicated in FIG. 18, exemplary statistical techniques 1880 may be used for optimizing therapy.

Figure 19:
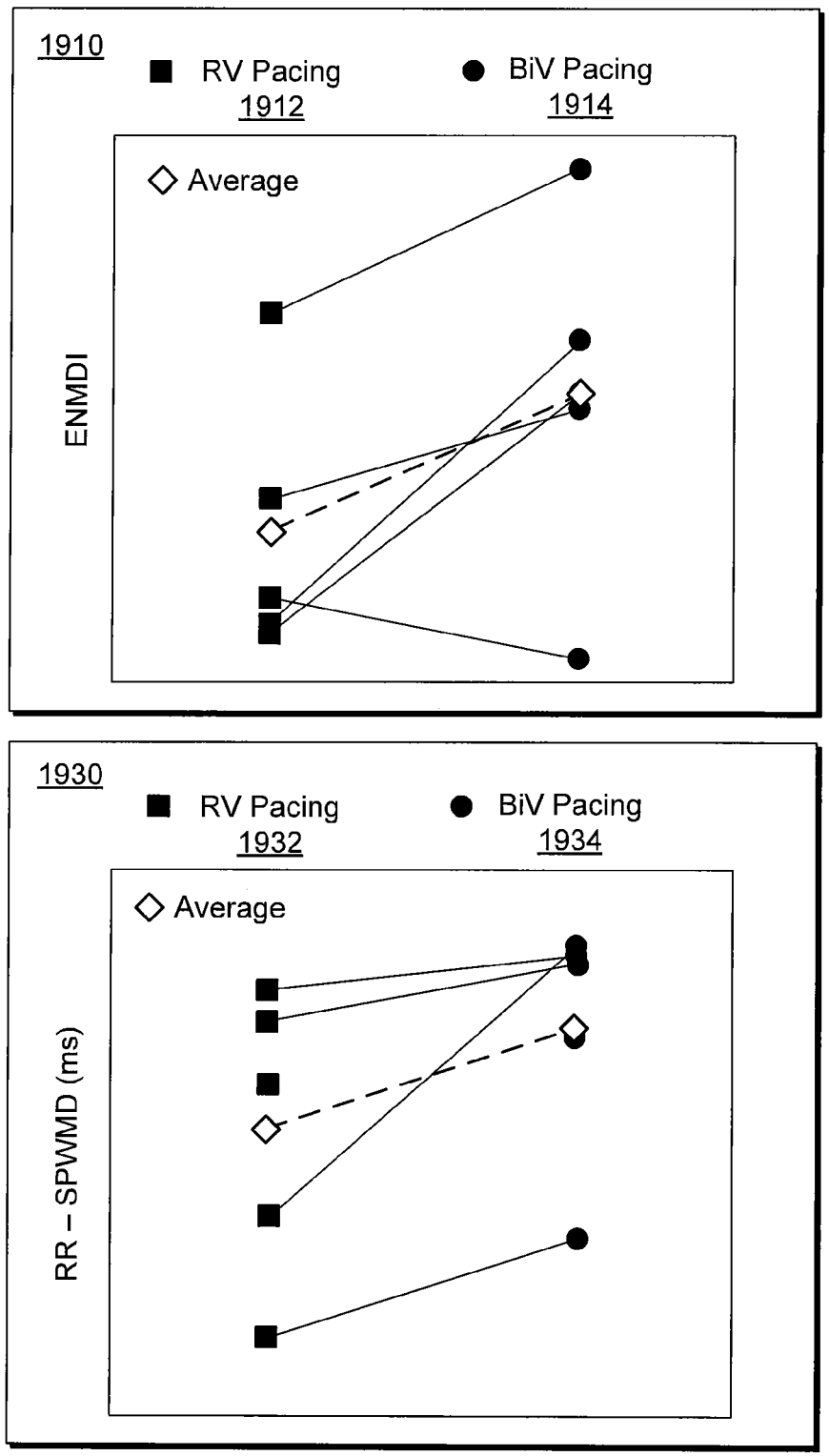
FIG. 19 is a diagram of echocardiographic data for right ventricular pacing and biventricular pacing scenarios of a validation technique to validated indexes and techniques.

FIG. 19 shows an exemplary validation technique 1905, which may be used to validate vector-based indexes, techniques, associated methods (see, e.g., FIG. 18). The validation technique 1905 relies on echocardiographic data, as shown in a plot 1910 of ENSITE® system mechanical dyssynchrony index (ENMDI) data and a plot 1930 of septal to posterior wall motion delay (SPWMD) data. The plot 1910 includes RV pacing data 1912 and biventricular pacing data 1914. Similarly, the plot 1930 includes RV pacing data 1932 and biventricular pacing data 1934. These data indicate that various exemplary dyssynchrony indexes (based on vector analysis) correlate with echocardiograph data, for a group of five patients; noting that in all but one patient, biventricular pacing resulted in higher ENMDI and SPWMD values. In the particular example of FIG. 19, the ENMDI is computed as the zero-time lag coefficient of the cross-covariance (e.g., physiological or realtime "phase"); noting that one or more other coefficients may be analyzed (e.g., corresponding to phase shifts, etc.).

Exemplary External Programmer

Figure 20:
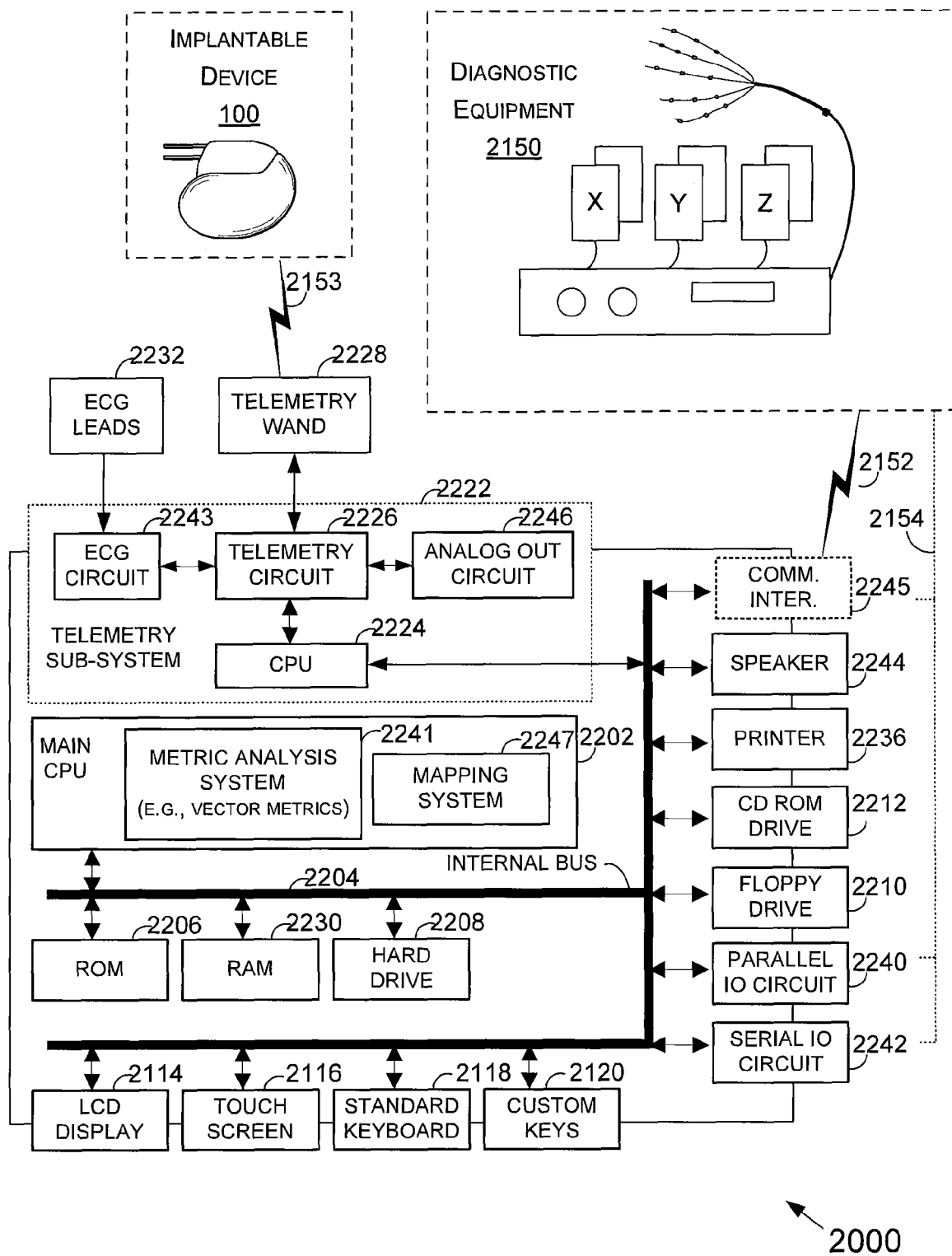
FIG. 20 is an exemplary system for acquiring information and analyzing information to assess stability of an electrode, a lead or implanted device.

FIG. 20 illustrates pertinent components of an external programmer 2000 for use in programming an implantable medical device 100 (see, e.g., FIGS. 1 and 2). The external programmer 2000 optionally receives information from other diagnostic equipment 2150, which may be a computing device capable of acquiring location information and other information. For example, the equipment 2150 may include a computing device to deliver current and to measure potentials using a variety of electrodes including at least one electrode positionable in the body (e.g., in a vessel, in a chamber of the heart, within the pericardium, etc.). Equipment may include a lead for chronic implantation or a catheter for temporary implantation in a patient's body. Equipment may allow for acquisition of respiratory motion and aid the programmer 2000 in distinguishing respiratory motion from cardiac.

Briefly, the programmer 2000 permits a clinician or other user to program the operation of the implanted device 100 and to retrieve and display information received from the implanted device 100 such as IEGM data and device diagnostic data. Where the device 100 includes a module such as the position and/or metrics module 239, then the programmer 2000 may instruct the device 100 to measure potentials and to communicate measured potentials to the programmer via a communication link 2153. The programmer 2000 may also instruct a device or diagnostic equipment to deliver current to generate one or more potential fields within a patient's body where the implantable device 100 may be capable of measuring potentials associated with the field(s).

The external programmer 2000 may be configured to receive and display ECG data from separate external ECG leads 2232 that may be attached to the patient. The programmer 2000 optionally receives ECG information from an ECG unit external to the programmer 2000. As already mentioned, the programmer 2000 may use techniques to account for respiration.

Depending upon the specific programming, the external programmer 2000 may also be capable of processing and analyzing data received from the implanted device 100 and from ECG leads 2232 to, for example, render diagnosis as to medical conditions of the patient or to the operations of the implanted device 100. As noted, the programmer 2000 is also configured to receive data representative of conduction time delays from the atria to the ventricles and to determine, therefrom, an optimal or preferred location for pacing. Further, the programmer 2000 may receive information such as ECG information, IEGM information, information from diagnostic equipment, etc., and determine one or more metric (e.g., consider the method 300 of FIG. 3, the method 400 of FIG. 4, etc.).

Now, considering the components of programmer 2000, operations of the programmer are controlled by a CPU 2202, which may be a generally programmable microprocessor or microcontroller or may be a dedicated processing device such as an application specific integrated circuit (ASIC) or the like. Software instructions to be performed by the CPU 2202 are accessed via an internal bus 2204 from a read only memory (ROM) 2206 and random access memory 2230. Additional software may be accessed from a hard drive 2208, floppy drive 2210, and CD ROM drive 2212, or other suitable permanent or removable mass storage device. Depending upon the specific implementation, a basic input output system (BIOS) is retrieved from the ROM 2206 by CPU 2202 at power up. Based upon instructions provided in the BIOS, the CPU 2202 "boots up" the overall system in accordance with well-established computer processing techniques.

Once operating, the CPU 2202 displays a menu of programming options to the user via an LCD display 2114 or other suitable computer display device. To this end, the CPU 2202 may, for example, display a menu of specific programming parameters of the implanted device 100 to be programmed or may display a menu of types of diagnostic data to be retrieved and displayed. In response thereto, the clinician enters various commands via either a touch screen 2116 overlaid on the LCD display or through a standard keyboard 2118 supplemented by additional custom keys 2120, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

With regard to the determination of location stability (e.g., for pacing, sensing, etc.), CPU 2202 includes a metric analysis system 2241 and a 3-D mapping system 2247. The systems 2241 and 2247 may receive information from the implantable device 100 and/or diagnostic equipment 2150. The metric analysis system 2241 optionally includes control logic to associate information and to make one or more conclusions based on a metric or metrics (e.g., consider the block 430 of FIG. 4).

Where information is received from the implanted device 100, a telemetry wand 2228 may be used. Other forms of wireless communication exist as well as forms of communication where the body is used as a "wire" to communicate information from the implantable device 100 to the programmer 2000.

If information is received directly from diagnostic equipment 2150, any appropriate input may be used, such as parallel IO circuit 2240 or serial IO circuit 2242. Motion information received via the device 100 or via other diagnostic equipment 2150 may be analyzed using the mapping system 2247. In particular, the mapping system 2247 (e.g., control logic) may identify positions within the body of a patient and associate such positions with one or more electrodes where such electrodes may be capable of delivering stimulation energy to the heart.

A communication interface 2245 optionally allows for wired or wireless communication with diagnostic equipment 2150 or other equipment. The communication interface 2245 may be a network interface connected to a network (e.g., intranet, Internet, etc.).

A map or model of cardiac motion may be displayed using display 2114 based, in part, on 3-D heart information and optionally 3-D torso information that facilitates interpretation of motion information. Such 3-D information may be input via ports 2240, 2242, 2245 from, for example, a database, a 3-D imaging system, a 3-D location digitizing apparatus (e.g., stereotactic localization system with sensors and/or probes) capable of digitizing the 3-D location. According to such an example, a clinician can thereby view the stability of a location on a map of the heart to ensure that the location is acceptable before an electrode or electrodes are positioned and optionally fixed at that location. While 3-D information and localization are mentioned, information may be provided with fewer dimensions (e.g., 1-D or 2-D). For example, where motion in one dimension is insignificant to one or more other dimensions, then fewer dimensions may be used, which can simplify procedures and reduce computing requirements of a programmer, an implantable device, etc. The programmer 2000 optionally records procedures and allows for playback (e.g., for subsequent review). For example, a heart map and all of the electrical activation data, mechanical activation data, parameter data, etc., may be recorded for subsequent review, perhaps if an electrode needs to be repositioned or one or more other factors need to be changed (e.g., to achieve an optimal configuration). Electrodes may be lead based or non-lead based, for example, an implantable device may operate as an electrode and be self powered and controlled or be in a slave-master relationship with another implantable device (e.g., consider a satellite pacemaker, etc.). An implantable device may use one or more epicardial electrodes.

Once all pacing leads are mounted and all pacing devices are implanted (e.g., master pacemaker, satellite pacemaker, biventricular pacemaker), the various devices are optionally further programmed.

The telemetry subsystem 2222 may include its own separate CPU 2224 for coordinating the operations of the telemetry subsystem. In a dual CPU system, the main CPU 2202 of programmer communicates with telemetry subsystem CPU 2224 via internal bus 2204. Telemetry subsystem additionally includes a telemetry circuit 2226 connected to telemetry wand 2228, which, in turn, receives and transmits signals electromagnetically from a telemetry unit of the implanted device. The telemetry wand is placed over the chest of the patient near the implanted device 100 to permit reliable transmission of data between the telemetry wand and the implanted device.

Typically, at the beginning of the programming session, the external programming device 2000 controls the implanted device(s) 100 via appropriate signals generated by the telemetry wand to output all previously recorded patient and device diagnostic information. Patient diagnostic information may include, for example, motion information (e.g., cardiac, respiratory, etc.) recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like.

Data retrieved from the implanted device(s) 100 can be stored by external programmer 2000 (e.g., within a random access memory (RAM) 2230, hard drive 2208, within a floppy diskette placed within floppy drive 2210). Additionally, or in the alternative, data may be permanently or semi-permanently stored within a compact disk (CD) or other digital media disk, if the overall system is configured with a drive for recording data onto digital media disks, such as a write once read many (WORM) drive. Where the programmer 2000 has a communication link to an external storage device or network storage device, then information may be stored in such a manner (e.g., on-site database, off-site database, etc.). The programmer 2000 optionally receives data from such storage devices.

A typical procedure may include transferring all patient and device diagnostic data stored in an implanted device 100 to the programmer 2000. The implanted device(s) 100 may be further controlled to transmit additional data in real time as it is detected by the implanted device(s) 100, such as additional motion information, IEGM data, lead impedance data, and the like. Additionally, or in the alternative, telemetry subsystem 2222 receives ECG signals from ECG leads 2232 via an ECG processing circuit 2234. As with data retrieved from the implanted device 100, signals received from the ECG leads are stored within one or more of the storage devices of the programmer 2000. Typically, ECG leads output analog electrical signals representative of the ECG. Accordingly, ECG circuit 2234 includes analog to digital conversion circuitry for converting the signals to digital data appropriate for further processing within programmer 2000. Depending upon the implementation, the ECG circuit 2243 may be configured to convert the analog signals into event record data for ease of processing along with the event record data retrieved from the implanted device. Typically, signals received from the ECG leads 2232 are received and processed in real time.

Thus, the programmer 2000 is configured to receive data from a variety of sources such as, but not limited to, the implanted device 100, the diagnostic equipment 2150 and directly or indirectly via external ECG leads (e.g., subsystem 2222 or external ECG system). The diagnostic equipment 2150 includes wired 2154 and/or wireless capabilities 2152 which optionally operate via a network that includes the programmer 2000 and the diagnostic equipment 2150 or data storage associated with the diagnostic equipment 2150.

Data retrieved from the implanted device(s) 100 typically includes parameters representative of the current programming state of the implanted devices. Under the control of the clinician, the external programmer displays the current programming parameters and permits the clinician to reprogram the parameters. To this end, the clinician enters appropriate commands via any of the aforementioned input devices and, under control of CPU 2202, the programming commands are converted to specific programming parameters for transmission to the implanted device 100 via telemetry wand 2228 to thereby reprogram the implanted device 100 or other devices, as appropriate.

Prior to reprogramming specific parameters, the clinician may control the external programmer 2000 to display any or all of the data retrieved from the implanted device 100, from the ECG leads 2232, including displays of ECGs, IEGMs, statistical patient information (e.g., via a database or other source), diagnostic equipment 2150, etc. Any or all of the information displayed by programmer may also be printed using a printer 2236.

A wide variety of parameters may be programmed by a clinician. In particular, for CRT, the AV delay and the VV delay of the implanted device(s) 100 are set to optimize cardiac function. In one example, the VV delay is first set to zero while the AV delay is adjusted to achieve the best possible cardiac function, optionally based on motion information. Then, VV delay may be adjusted to achieve still further enhancements in cardiac function.

Programmer 2000 optionally includes a modem to permit direct transmission of data to other programmers via the public switched telephone network (PSTN) or other interconnection line, such as a T1 line or fiber optic cable. Depending upon the implementation, the modem may be connected directly to internal bus 2204 may be connected to the internal bus via either a parallel port 2240 or a serial port 2242.

Other peripheral devices may be connected to the external programmer via the parallel port 2240, the serial port 2242, the communication interface 2245, etc. Although one of each is shown, a plurality of input output (IO) ports might be provided. A speaker 2244 is included for providing audible tones to the user, such as a warning beep in the event improper input is provided by the clinician. Telemetry subsystem 2222 additionally includes an analog output circuit 2246 for controlling the transmission of analog output signals, such as IEGM signals output to an ECG machine or chart recorder.

With the programmer 2000 configured as shown, a clinician or other user operating the external programmer is capable of retrieving, processing and displaying a wide range of information received from the ECG leads 2232, from the implanted device 100, the diagnostic equipment 2150, etc., and to reprogram the implanted device 100 or other implanted devices if needed. The descriptions provided herein with respect to FIG. 20 are intended merely to provide an overview of the operation of programmer and are not intended to describe in detail every feature of the hardware and software of the device and is not intended to provide an exhaustive list of the functions performed by the device.

Conclusion

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A method comprising:
   selecting a first pair of electrodes to define a first vector and selecting a second pair of electrodes to define a second vector;
   for each of the first and second pairs of electrodes, acquiring coordinate position information at each of a plurality of fiducials within a cardiac cycle, wherein the acquiring comprises establishing an electrical localization field in the patent and using each of the electrodes for measuring one or more electrical potentials in the electrical localization field; and
   determining a first vector metric based on the acquired coordinate position information for the first pair of electrodes, and determining a second vector metric based on the acquired coordinate position information for the second pair of electrodes.

2. The method of claim 1 wherein the first and second vector metrics comprise a measure of vector magnitude as a function of time during at least a portion of the cardiac cycle.

3. The method of claim 1 wherein the first and second vector metrics comprise a measure of vector angle as a function of time during at least a portion of the cardiac cycle.

4. The method of claim 2 wherein the measure of vector magnitude comprises a waveform plot of vector magnitude as a function of time.

5. The method of claim 3 wherein the measure of vector angle comprises a waveform plot of vector angles as a function of time.

6. The method of claim 1 wherein each of the first vector and the second vector originates with respect to a first chamber of a heart and terminates with respect to a respective second chamber of the heart different from the first chamber.

7. The method of claim 6 wherein the first chamber is a right atrium.

8. The method of claim 7 wherein the second chamber of the first vector is a right ventricle and the second chamber of the second vector is a left ventricle.

9. The method of claim 6 wherein the first chamber is a right ventricle.

10. The method of claim 9 wherein the second chamber of the first vector is a right atrium and the second chamber of the second vector is a left ventricle.

11. The method of claim 6 wherein the first chamber is a left ventricle.

12. The method of claim 11 wherein the second chamber of the first vector is a right atrium and the second chamber of the second vector is a right ventricle.

13. The method of claim 1 further comprising determining a dyssynchrony index based on the first vector metric and the second vector metric.

14. The method of claim 13 wherein the first and second vector metrics comprise a measure of vector magnitude as a function of time during at least a portion of the cardiac cycle, and determining a dyssynchrony index comprises at least one of:
    determining a peak-to-peak value;
    determining a maximum; and
    determining an average slope.

15. The method of claim 13 wherein the first and second vector metrics comprise a waveform plot of vector magnitude as a function of time during at least a portion of the cardiac cycle, and determining a dyssynchrony index further comprises:
    calculating an area under the vector magnitude waveform; and
    calculating at least one of a difference between the two areas or a quotient of the two areas.

16. The method of claim 1 wherein the first pair of electrodes and the second pair of electrodes include a same electrode.

17. One or more non-transitory computer-readable storage media comprising processor-executable instructions to configure a computing device to:
    select a first pair of electrodes to define a first vector and selecting a second pair of electrodes to define a second vector;
    for each of the first and second pairs of electrodes, acquire coordinate position information at each of a plurality of fiducial points within a cardiac cycle, wherein the acquiring comprises establishing an electrical localization field in the patent and using each of the electrodes for measuring one or more electrical potentials in the electrical localization field; and
    determine a first vector metric based on the acquired coordinate position information for the first pair of electrodes, and determining a second vector metric based on the acquired coordinate position information for the second pair of electrodes.

18. The media of claim 17 wherein each of the first vector and the second vector originates with respect to a first chamber of a heart and terminates with respect to a respective second chamber of the heart different from the first chamber.

* * * * *